(12) United States Patent
Ross et al.

(10) Patent No.: US 10,677,764 B2
(45) Date of Patent: Jun. 9, 2020

(54) TEMPERATURE ESTIMATION AND TISSUE DETECTION OF AN ULTRASONIC DISSECTOR FROM FREQUENCY RESPONSE MONITORING

(71) Applicant: Covidien LP, Mansfield, MA (US)

(72) Inventors: Anthony B. Ross, Boulder, CO (US); David J. Van Tol, Boulder, CO (US); David Price, Portland, OR (US)

(73) Assignee: COVIDIEN LP, Mansfield, MA (US)

( * ) Notice: Subject to any disclaimer, the term of this patent is extended or adjusted under 35 U.S.C. 154(b) by 1549 days.

(21) Appl. No.: 13/840,432

(22) Filed: Mar. 15, 2013

(65) Prior Publication Data

US 2013/0331874 A1 Dec. 12, 2013

Related U.S. Application Data

(60) Provisional application No. 61/658,067, filed on Jun. 11, 2012, provisional application No. 61/658,045, (Continued)

(51) Int. Cl.
  *G01N 29/44* (2006.01)
  *A61B 17/32* (2006.01)
  *A61B 17/00* (2006.01)

(52) U.S. Cl.
  CPC ..... *G01N 29/44* (2013.01); *A61B 17/320092* (2013.01); *A61B 2017/0003* (2013.01); (Continued)

(58) Field of Classification Search
  CPC ............ A61B 17/32; A61B 17/320016; A61B 17/320068; A61B 17/320092; G01N 29/44
  See application file for complete search history.

(56) References Cited

U.S. PATENT DOCUMENTS

| 4,646,754 A | * | 3/1987 | Seale | ........................ A61B 3/16 600/402 |
| 5,001,649 A | | 3/1991 | Lo et al. | |

(Continued)

FOREIGN PATENT DOCUMENTS

| JP | S63212342 A | 9/1988 |
| JP | H0751281 A | 2/1995 |

(Continued)

OTHER PUBLICATIONS

Ching-Ping Janet Shen, Silicon Based Co-Integrated Bioelectrical and Biomechanical Interfaces: Applications to Insect Olfactory Neural Interfaces, Miniature Neural Interfaces, and Cardiac Excitation Characterization, Jan. 2012, PH. D. Thesis, Graduate School of Cornell University, 184 pp. (Year: 2012).*

(Continued)

*Primary Examiner* — Toan M Le

(74) *Attorney, Agent, or Firm* — Carter, DeLuca & Farrell LLP

(57) ABSTRACT

An ultrasonic surgical apparatus and method, the apparatus including a signal generator outputting a drive signal having a frequency, an oscillating structure, receiving the drive signal and oscillating at the frequency of the drive signal, and a bridge circuit, detecting the mechanical motion of the oscillating structure and outputting a signal representative of the mechanical motion. The ultrasonic surgical apparatus also includes a microcontroller receiving the signal output by the bridge circuit, the microcontroller determining an instantaneous frequency at which the oscillating structure is oscillating based on the received signal, and determining a frequency adjustment necessary to maintain the oscillating structure oscillating at its resonance frequency, the microcontroller further determining the quality (Q value) of the (Continued)

signal received from the bridge circuit and determining material type contacting the oscillating structure.

17 Claims, 15 Drawing Sheets

Related U.S. Application Data filed on Jun. 11, 2012, provisional application No. 61/658,081, filed on Jun. 11, 2012.

(52) U.S. Cl.
CPC .............. *A61B 2017/00075* (2013.01); *A61B 2017/00084* (2013.01); *A61B 2017/00106* (2013.01); *A61B 2017/00734* (2013.01); *A61B 2017/320094* (2017.08); *A61B 2017/320095* (2017.08)

(56) References Cited

U.S. PATENT DOCUMENTS

| | | | |
|---|---|---|---|
| 5,185,585 A | 2/1993 | Newell et al. | |
| 5,406,503 A | 4/1995 | Williams, Jr. et al. | |
| 5,449,370 A | 9/1995 | Vaitekunas | |
| 6,995,622 B2 | 2/2006 | Partridge et al. | |
| 7,134,341 B2 | 11/2006 | Girmonsky et al. | |
| 7,165,451 B1 | 1/2007 | Brooks et al. | |
| 7,221,230 B2 | 5/2007 | Partridge et al. | |
| 7,224,236 B2 | 5/2007 | Partridge et al. | |
| RE40,709 E | 5/2009 | Akahane et al. | |
| 8,061,014 B2 | 11/2011 | Smith et al. | |
| 2005/0020967 A1 | 1/2005 | Ono | |
| 2005/0070800 A1 | 3/2005 | Takahashi | |
| 2007/0016235 A1 | 1/2007 | Tanaka et al. | |
| 2008/0015620 A1 | 1/2008 | Friedman et al. | |
| 2009/0036913 A1 | 2/2009 | Wiener et al. | |
| 2009/0036914 A1 | 2/2009 | Houser | |
| 2009/0143804 A1 | 6/2009 | Palmer et al. | |
| 2010/0292573 A1 | 11/2010 | Tanaka | |
| 2011/0009890 A1 | 1/2011 | Palmer et al. | |
| 2011/0082486 A1 | 4/2011 | Messerly et al. | |
| 2011/0241786 A1 | 10/2011 | Gilbert | |
| 2012/0136279 A1 | 5/2012 | Tanaka et al. | |
| 2013/0289591 A1* | 10/2013 | Boudreaux | A61B 17/32006 606/169 |

FOREIGN PATENT DOCUMENTS

| | | |
|---|---|---|
| JP | 2003-000610 A | 1/2003 |
| JP | 2005027907 A | 2/2005 |
| JP | 2011505226 A | 2/2011 |
| JP | 2011-087937 A | 5/2011 |
| WO | 2009/073608 A1 | 6/2009 |
| WO | 102008054083 | 5/2010 |
| WO | 2010134484 A1 | 11/2010 |

OTHER PUBLICATIONS

European Search Report corresponding to European Application No. EP 13 17 1419.8-1659, dated Feb. 17, 2014; 9 pages.
European Search Report corresponding to European Application No. EP 13 17 1420.6-1659, dated Feb. 17, 2014; 8 pages.
European Search Report corresponding to European Application No. EP 13 17 1421.4-1659, dated Feb. 17, 2014; 8 pages.
European Examination Report in corresponding EP Application No. 13171419.8, dated Jan. 27, 2017, 7 pages.
Japanese OA issued in corresponding JP Application No. 2013-120606 dated Mar. 2, 2017, 6 pages.
Australian OA issued in corresponding Application No. 2013205878 dated Mar. 15, 2017, 3 pages.
Notice of Allowance for Japanese Application No. 2013-120606 dated Aug. 10, 2017.
Canadian Office Action issued by the Canadian Intellectual Property Office dated Mar. 12, 2019 in corresponding Canadian Patent Application No. 2,816,208.

* cited by examiner

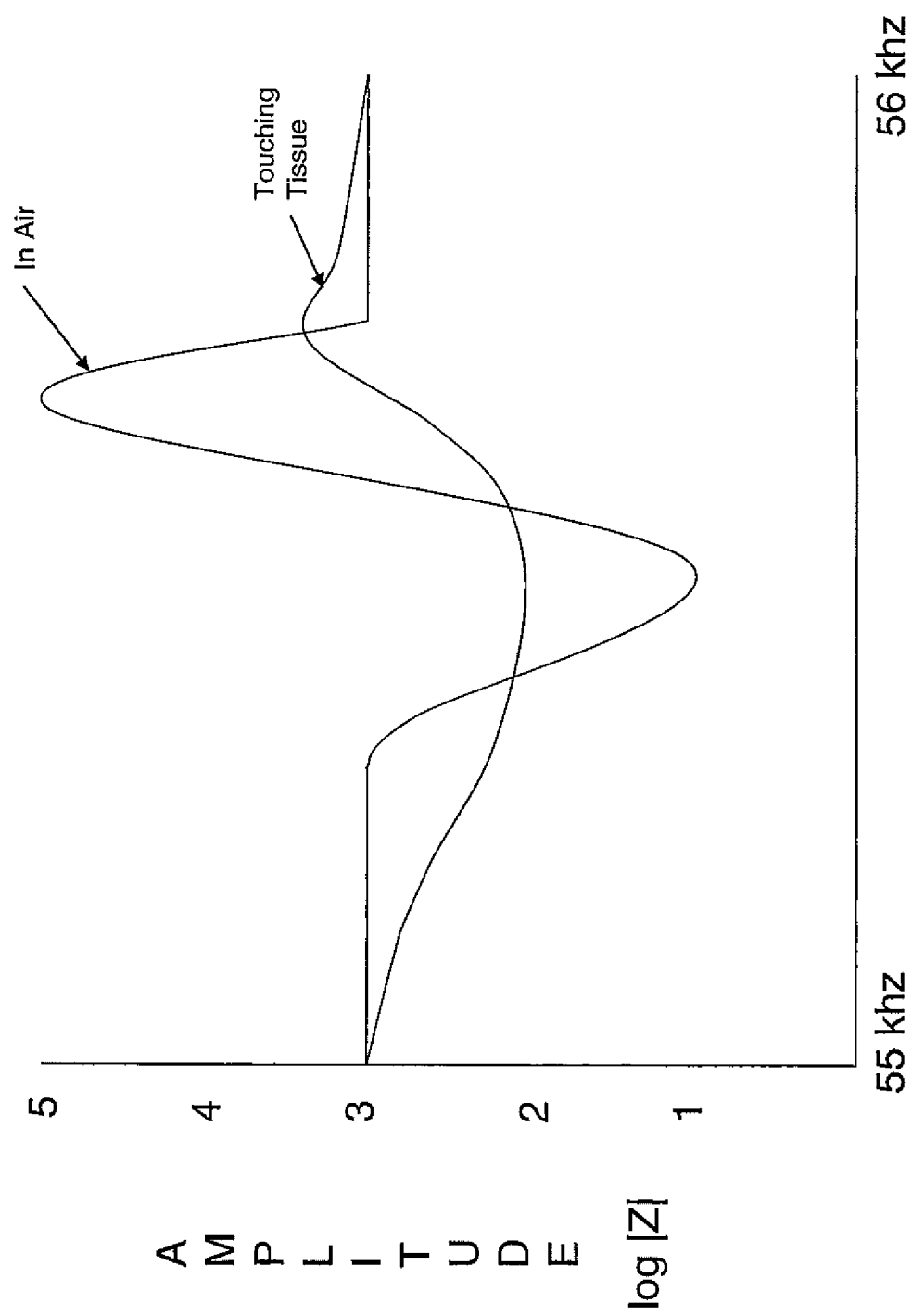

TEMPERATURE ESTIMATION AND TISSUE DETECTION OF AN ULTRASONIC DISSECTOR FROM FREQUENCY RESPONSE MONITORING

CROSS REFERENCE TO RELATED APPLICATIONS

This application claims the benefit of U.S. Provisional Patent Application Ser. No. 61/658,067 filed Jun. 11, 2012; U.S. Provisional Patent Application Ser. No. 61/658,045 filed Jun. 11, 2012; and U.S. Provisional Patent Application Ser. No. 61/658,081 filed Jun. 11, 2012. The entire contents of these cross-referenced applications are incorporated by reference herein.

BACKGROUND

1. Technical Field

The present disclosure relates generally to an ultrasonic surgical instrument and, more particularly, relates to estimating the temperature of the ultrasonic surgical instrument and distinguishing the type of tissue engaged by the ultrasonic surgical instrument.

2. Background of the Related Art

Ultrasonic instruments are effectively used in the treatment of many medical conditions, such as removal of tissue and the cauterization and sealing of vessels. Cutting instruments that utilize ultrasonic waves generate vibrations with an ultrasonic transducer along a longitudinal axis of a cutting blade. By placing a resonant wave along the length of the blade, high-speed longitudinal mechanical movement is produced at the end of the blade. These instruments are advantageous because the mechanical vibrations transmitted to the end of the blade are very effective at cutting organic tissue and, simultaneously, coagulate the tissue using the heat energy produced by the ultrasonic frequencies. Such instruments are particularly well suited for use in minimally invasive procedures, such as endoscopic or laparoscopic procedures, where the blade is passed through a trocar to reach the surgical site.

For each kind of cutting blade (e.g., length, material, size), there are one or more (periodic) drive signals that produce a resonance along the length of the blade. Resonance results in optimal movement of the blade tip and, therefore, optimal performance during surgical procedures. However, producing an effective cutting-blade drive signal is not a trivial task. For instance, the frequency, current, and voltage applied to the cutting tool must all be controlled dynamically, as these parameters change with the varying load placed on the blade and with temperature differentials that result from use of the tool.

Detection of the temperature of the cutting blade and other points along an ultrasonic surgical instrument can be useful for a variety of reasons, including use as a feedback mechanism for control of the ultrasonic instrument. Moreover, because ultrasonic instruments of the type contemplated by this disclosure may be used in endoscopic and laparoscopic surgeries, where the surgeon's ability to sense what is happening at the blade of the ultrasonic instrument is limited, providing temperature information ensures necessary procedures may be employed by the surgeon to achieve optimal surgical results.

Temperature measurements have traditionally been taken by thermocouples placed near the blade at the distal end of the surgical instrument. However, thermocouples require separate attachment to the ultrasonic surgical instrument, which can present problems. Even when attached, thermocouples require at minimum two wires (comprised at least in part of dissimilar metals) leading from the hot junction of the thermocouple along the length of the device to a volt-meter and processing components.

Current systems for identifying tissue rely on either high cost scanning mechanisms including ultrasound, CAT, and MRI, or lower cost, but limited to field of view, methods such as optical imaging through a laparoscope.

Thus, there is a need for improved methods of temperature detection of an ultrasonic surgical instrument and further a need for improved methods of tissue type detection.

SUMMARY

One aspect of the present disclosure is directed to an ultrasonic surgical apparatus including a signal generator outputting a drive signal having a frequency, an oscillating structure, receiving the drive signal and oscillating at the frequency of the drive signal, and a bridge circuit, detecting the mechanical motion of the oscillating structure and outputting a signal representative of the mechanical motion. The ultrasonic surgical apparatus also includes a microcontroller receiving the signal output by the bridge circuit, the microcontroller determining an instantaneous frequency at which the oscillating structure is oscillating based on the received signal, and determining a frequency adjustment necessary to maintain the oscillating structure oscillating at its resonance frequency, the microcontroller further determining the quality (Q value) of the signal received from the bridge circuit and determining material type contacting the oscillating structure.

According to a further aspect of the disclosure the determined Q value is compared to Q values stored in memory to determine the material in contact with the oscillating structure. The Q values stored in memory distinguishes between material types selected from the group consisting of wet tissue, dry tissue, dense tissue, bone, and metal objects. The determined Q value may take into account clamping pressure applied to the material by an end effector at the end of the oscillating structure. Further the detected specific Q value may result in a determination that a blade portion of the ultrasonic surgical apparatus is contacting an end effector of the oscillating structure.

A further aspect of the present disclosure is directed to a method of determining the determining the type of material an ultrasonic surgical apparatus is contacting including generating a drive signal and supplying the drive signal to an oscillating structure, detecting the mechanical motion of the oscillating structure and generating a signal representative of the mechanical motion, and processing the signal representative of the mechanical motion to determine determining an instantaneous frequency at which the oscillating structure is oscillating based on the received signal. The method also includes generating a frequency adjustment necessary to maintain the oscillating structure oscillating at its resonance frequency; and determining the quality (Q value) of the signal received from the bridge circuit to identify the material contacting the oscillating structure.

According to a further aspect of the present disclosure the determined Q value is compared to Q values stored in memory to determine the material in contact with the oscillating structure. The Q values may be stored in memory and distinguish between material types selected from the group consisting of wet tissue, dry tissue, dense tissue, bone, and metal objects. Further the determined Q value may take into account clamping pressure applied to the material by an end effector at the end of the oscillating structure. Still further upon detecting a specific Q value the ultrasonic surgical apparatus may determine that a blade portion of the ultrasonic surgical apparatus is contacting an end effector of the ultrasonic surgical apparatus.

BRIEF DESCRIPTION OF THE DRAWINGS

Various embodiments of the subject instrument are described herein with reference to the drawings wherein:

FIG. 17 is a Bode plot depicting the difference in Q of an ultrasonic surgical instrument when operating in air and when grasping tissue with respect to impedance in accordance with an exemplary embodiment of the present disclosure.

DETAILED DESCRIPTION

Figure 1:
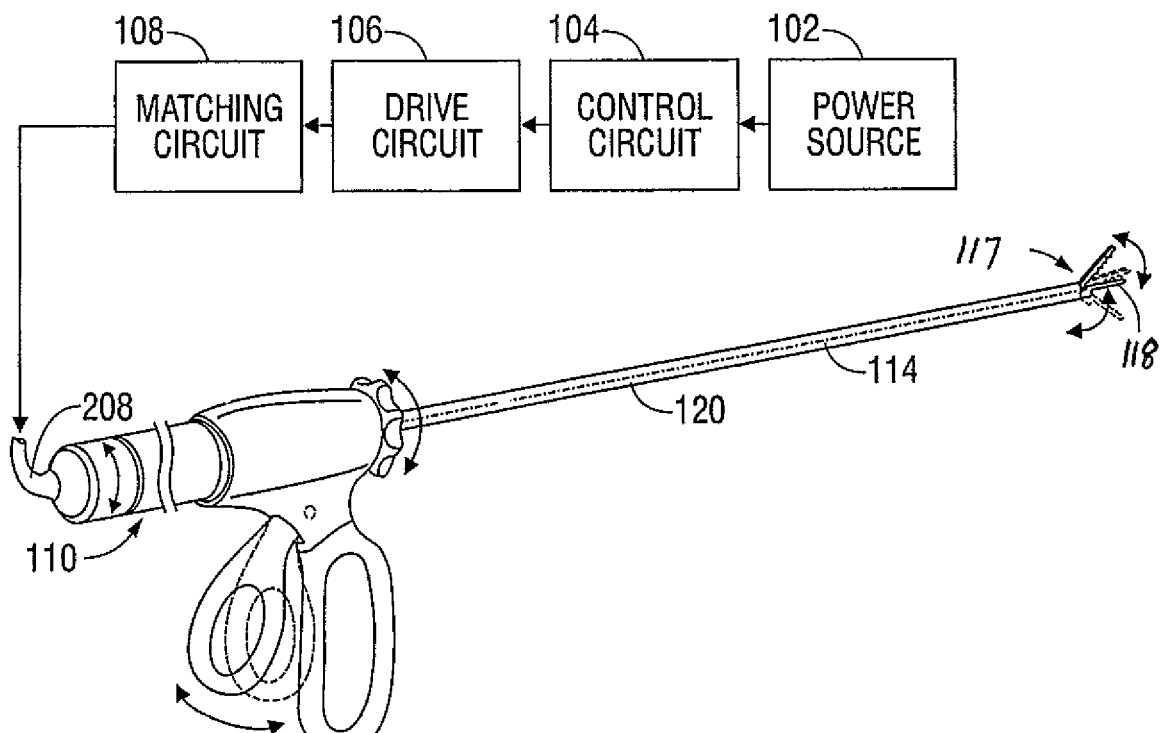
FIG. 1 is a diagrammatic illustration of components of an ultrasonic surgical system with separate power, control, drive and matching components in block diagram form.

Particular embodiments of the present disclosure are described herein below with reference to the accompanying drawings. In the following description, well-known functions or constructions are not described in detail to avoid obscuring the present disclosure in unnecessary detail.

It is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting; but rather, to provide an understandable description of the disclosure.

Before the present disclosure is disclosed and described, it is to be understood that the terminology used herein is for the purpose of describing particular embodiments only and is not intended to be limiting. In this document, the terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described. Finally, as used herein, the terms "distal" and "proximal" are considered from the vantage of the user or surgeon, thus the distal end of a surgical instrument is that portion furthest away from the surgeon when in use, and the proximal end is that portion generally closest to the user.

It will be appreciated that embodiments of the disclosure described herein may be comprised of one or more conventional processors and unique stored program instructions that control the one or more processors to implement, in conjunction with certain non-processor circuits and other elements, some, most, or all of the functions of ultrasonic surgical instruments described herein. The non-processor circuits may include, but are not limited to, signal drivers, clock circuits, power source circuits, and user input and output elements. Alternatively, some or all functions could be implemented by a state machine that has no stored program instructions, in one or more application specific integrated circuits (ASICs), in which each function or some combinations of certain of the functions are implemented as custom logic, or in a field-programmable gate array (FPGA) enabling the use of updateable custom logic either by the manufacturer or the user. Of course, a combination of the three approaches could also be used. Thus, methods and means for these functions have been described herein.

The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

FIG. 1 shows a block schematic diagram of a known circuit used for applying ultrasonic mechanical movements to an end effector. The circuit includes a power source 102, a control circuit 104, a drive circuit 106, a matching circuit 108, a transducer 110, and also includes a handpiece 112, and a waveguide 114 secured to the handpiece 112 (diagrammatically illustrated by a dashed line) and supported by a cannula 120. The waveguide 114 terminates to a blade 118 at a distal end thereof. The transducer 110, waveguide 114, and blade 118 form an oscillating structure that generally resonates at the same frequency. A clamping mechanism referred to as an "end effector" 117, exposes and enables the blade portion 118 of the waveguide 114 to make contact with tissue and other substances. Commonly, the end effector 117 is a pivoting arm that acts to grasp or clamp onto tissue between the arm and the blade 118. However, in some devices, the end effector 117 is not present.

The drive circuit 104 produces a high-voltage self-oscillating signal. The high-voltage output of the drive circuit 104 is fed to the matching circuit 108, which contains signal-smoothing components that, in turn, produce a drive signal (wave) that is fed to the transducer 110. The oscillating input to the transducer 110 causes the mechanical portion of the transducer 110 to move back and forth at a magnitude and frequency that sets up a resonance along the waveguide 114. For optimal resonance and longevity of the resonating instrument and its components, the drive signal applied to the transducer 110 should be as smooth a sine wave as can practically be achieved. For this reason, the matching circuit 108, the transducer 110, and the waveguide 114 are selected to work in conjunction with one another and are all frequency sensitive with and to each other.

Because a relatively high-voltage (e.g., 100 V or more) is required to drive a typical piezoelectric transducer 110, one commonly used power source is an electric mains (e.g., a wall outlet) of, typically, up to 15 A, 120 VAC. Therefore, many known ultrasonic surgical instruments resemble that shown in FIGS. 1 and 2 and utilize a countertop box 202 with an electrical cord 204 to be plugged into the electrical mains 206 for supply of power. Resonance is maintained by a phase locked loop (PLL), which creates a closed loop between the output of the matching circuit 108 and the drive circuit 106. For this reason, in prior art devices, the countertop box 202 always has contained all of the drive and control electronics 104, 106 and the matching circuit(s) 108. A supply cord 208 delivers a sinusoidal waveform from the box 202 to the transducer 110 within the handpiece 112 and, thereby, to the waveguide 114. Resonance is often at varying waveguide 114 load conditions by monitoring and maintaining a constant current applied to the transducer.

Figure 3:
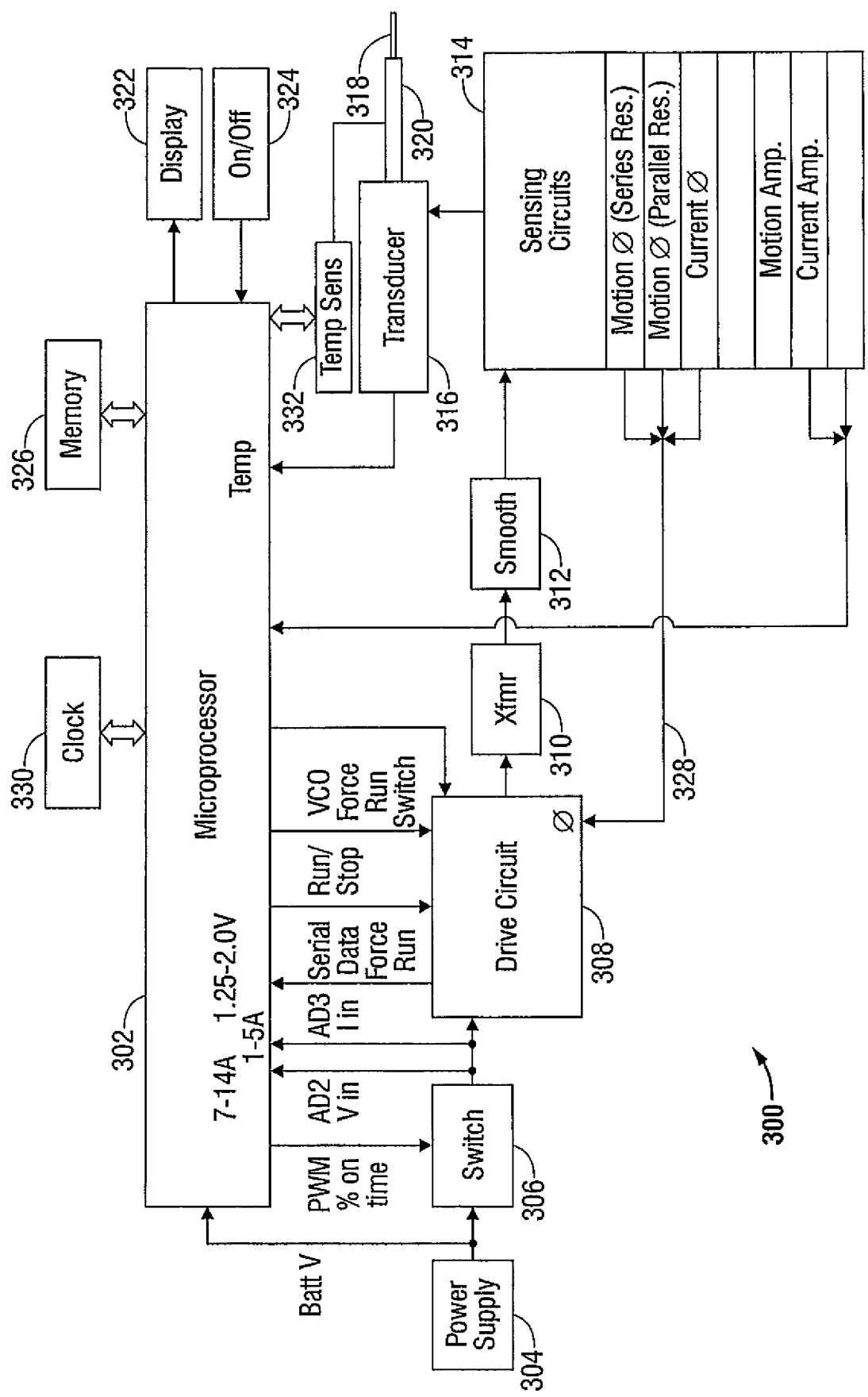
FIG. 3 is a block circuit diagram of an ultrasonic surgical instrument in accordance with an exemplary embodiment of the present disclosure.

FIG. 3 depicts a block diagram of an ultrasonic surgical instrument 300 according to one embodiment of the present disclosure. In FIG. 3 the ultrasonic surgical instrument 300 includes a microprocessor 302, a clock 330, a memory 326, a power supply 304 (e.g., a battery), a switch 306 (e.g., one or more a MOSFETs), a drive circuit 308 (PLL), a transformer 310, a signal smoothing circuit 312 (also referred to as a matching circuit and can be, e.g., a tank circuit), a sensing circuit 314, a transducer 316, and a waveguide 320, which terminates into an ultrasonic cutting blade 318. As used herein, the "waveguide-movement-generation assembly" is a sub-assembly including at least the transducer 316, but can also include other components, such as the drive circuit 308 (PLL), transformer 310, signal smoothing circuit 312, and/or the sensing circuit 314.

Figure 2:
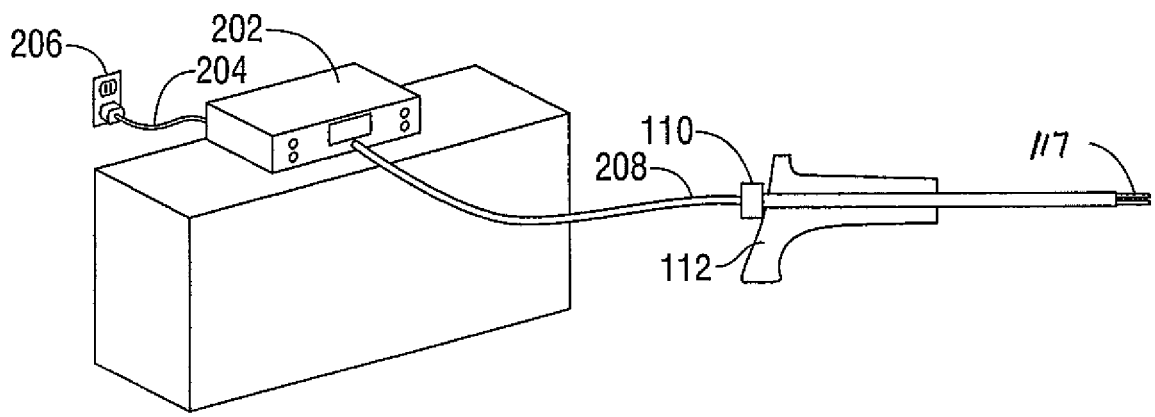
FIG. 2 is a diagram illustrating the ultrasonic surgical system of FIG. 1.

As an alternative to relying on AC mains 206 as depicted in FIG. 2, the embodiment shown in FIG. 3 employs power derived from only a battery, or a group of batteries, small enough to fit either within the handpiece 112 or within a small box that attaches to the user, for example, at a waistband. State-of-the-art battery technology provides powerful batteries of a few centimeters in height and width and a few millimeters in depth.

In the embodiment of FIG. 3, the output of the battery 304 is fed to and powers the processor 302. The processor 302 receives and outputs signals and, as will be described below, functions according to custom logic or in accordance with computer programs that are executed by the processor 302. The device 300 can also include a main memory 326, preferably, random access memory (RAM), that stores computer-readable instructions and data.

The output of the battery 304 also goes to a switch 306 that has a duty cycle controlled by the processor 302. By controlling the on-time for the switch 306, the processor 302 is able to dictate the total amount of power that is ultimately delivered to the transducer 316. In one embodiment, the switch 306 is an electrically controlled metal-oxide-semiconductor field-effect transistor (MOSFET), although other switches, field-effect transistors (FET's) and switching configurations are adaptable as well. Moreover, those of skill in the art will recognize that though described singularly, switch 306 may employ 2 or more MOSFETs. The output of the switch 306 is fed to a drive circuit 308 that contains, for example, a phase detecting PLL and/or a low-pass filter and/or a voltage-controlled oscillator. The output of the switch 306 is sampled by the processor 302 to determine the voltage and current of the output signal (referred to in FIG.

3 respectively as AD2 Vin and AD3 Iin). These values are used in a feedback architecture to adjust the pulse width modulation of the switch 306. For instance, the duty cycle of the switch 306 can vary from about 20% to about 80%, depending on the desired and actual output from the switch 306.

The drive circuit 308, which receives the signal from the switch 306, includes an oscillatory circuit that turns the output of the switch 306 into an electrical signal having a single ultrasonic frequency, e.g., 55 kHz (referred to as VCO in FIG. 3). As will be explained below, a smoothed-out version of this ultrasonic waveform is ultimately fed to the transducer 316 to produce a resonant sine wave along the waveguide 320. Resonance is achieved when current and voltage are substantially in phase at the input of the transducer 316. For this reason, the drive circuit 308 uses a PLL to sense the current and voltage input to the transducer 316 and to synchronize the current and voltage with one another. This sensing is performed over line 328, wherein the current phase is matched with a phase of the "motional" voltage and/or matches the input voltage phase with a phase of the "motional" current. The concept and technique of measuring motional voltage will be explained in detail below and in conjunction with the figures.

At the output of the drive circuit 308 is a transformer 310 able to step up the low voltage signal(s) to a higher voltage. It is noted that all upstream switching, prior to the transformer 310, has been performed at low (i.e., battery driven) voltages. This is at least partially due to the fact that the drive circuit 308 advantageously uses low on-resistance MOSFET switching devices. Low on-resistance MOSFET switches are advantageous, as they produce less heat than traditional MOSFET device and allow higher current to pass through. Therefore, the switching stage (pre transformer) can be characterized as low voltage/high current.

In one embodiment of the present disclosure, the transformer 310 steps up the battery voltage to 120V RMS. Transformers are known in the art and are, therefore, not explained here in detail. The output of the transformer 310 resembles a square wave 400, which waveform is undesirable because it is injurious to certain components, in particular, to the transducer 316. The square wave also generates interference between components. The matching circuit 312 of the present disclosure substantially reduces or eliminates these problems.

The wave shaping or matching circuit 312 sometimes referred to as a "tank circuit," smoothes the square wave output from the transformer 310 and turns the wave into a driving wave (e.g., a sine wave). The matching circuit 312, in one embodiment of the present disclosure, is a series L-C circuit and is controlled by the well-known principles of Kirchhoffs circuit laws. However, any matching circuit can be used here. The smooth sine wave 500 output from the matching circuit 312 is, then, fed to the transducer 316. Of course, other drive signals can be output from the matching circuit 312 that are not smooth sine waves.

A transducer 316 is an electromechanical device that converts electrical signals to physical movement, one example of such a device is formed of a stack of piezo-electric crystals. In a broader sense, a transducer 316 is sometimes defined as any device that converts a signal from one form to another. In the present disclosure, the driving wave (sine wave) is input to the transducer 316, which then imparts physical movements to the waveguide 320. As will be shown, this movement sets up a resonating wave on the waveguide 320, resulting in motion at the end of the waveguide 320.

In the exemplary embodiment where the transducer 316 is formed of a stack of piezo-electric crystals, each piezo-electric crystal is separated from the next by an insulator. The piezo-electric crystals change their longitudinal dimension with the simultaneous sinusoidal voltage applied to all the crystals such that the stack expands and contracts as a unit. These expansions and contractions are at the frequency of the drive signal produced by the driving circuit 308. The movement of the transducer 316 induces a sinusoidal wave along the length of the waveguide 320 thereby longitudinally moving the tip blade 318 the waveguide 320. The blade 318 tip is ideally at an "anti-node," as it is a moving point of the sine wave. The resulting movement of the waveguide 320 produces a "sawing" movement in the blade 318 at the end of the waveguide 320 providing a cutting motion that is able to slice easily through many materials, such as tissue and bone. The waveguide 320 also generates a great deal of frictional heat when so stimulated, which heat is conducted within the tissue that the waveguide 320 is cutting. This heat is sufficient to cauterize instantly blood vessels within the tissue being cut.

If the drive signal applied to the transducer 316 and traveling along the waveguide 320 is not at the resonant frequency for the ultrasonic surgical instrument, the last anti-node will not appear at the blade 318 of the waveguide 320. In such a case, the blade 318 of the waveguide 320 may move transverse to the longitudinal axis of the waveguide 320. While off resonant motion of the blade 318 is generally not desirable, in certain applications such off resonance motion may be desirable for certain periods of time and to achieve certain surgical outcomes.

The present disclosure utilizes the PLL in the drive circuit 308 to ensure that the movement of the waveguide 320 remains resonant along the waveguide 320 by monitoring the phase between the motional current and motional voltage waveforms fed to the transducer 316 and sending a correction signal back to the drive circuit 308. In certain embodiments, the transducer 316 may be cut in a different plane, thereby creating a torsional or twisting motion of the blade rather than only a sawing motion.

Figure 2A:
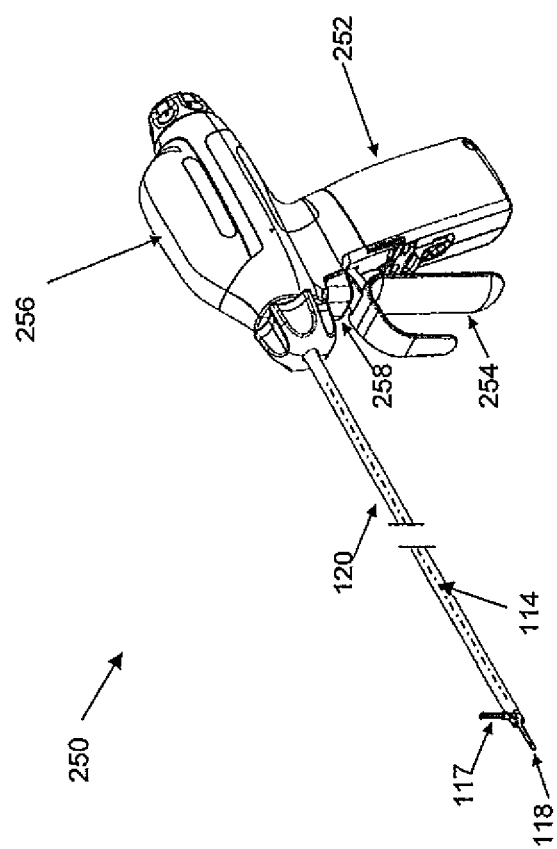
FIG. 2A is a diagram illustrating an ultrasonic surgical instrument in accordance with an exemplary embodiment of the present disclosure.

FIG. 2A depicts a further device in which embodiments of the present disclosure may be implemented, showing a battery operated hand held ultrasonic surgical device 250. As with the embodiments shown in FIGS. 1 and 2, the distal end (i.e. the end of the device furthest away from the user while in use) of the ultrasonic surgical instrument 250 includes an end effector 117 which incorporates a blade portion 118. The end effector 117 and blade 118 are formed at the distal end of the cannula 120 which encloses a waveguide 114, but formed within cannula 120, and connecting to the blade 118.

Power for the ultrasonic surgical device 250 is provided by a battery 252. In the example depicted in FIG. 2A the battery is formed as an integral component of the ultrasonic surgical device 250. Specifically the battery 252, when connected to the rest of the device, forms the handle. In an alternative arrangement the battery may be removably housed within a compartment of the handle. A variety of alternative arrangements for the battery and its incorporation into the ultrasonic surgical instrument 250 are described in detail in commonly assigned U.S. application Ser. No. 12/269,629, filed Nov. 12, 2008, and incorporated fully herein by reference. The battery itself is formed of one or more rechargeable cells. For example, the battery may include four cells connected in series having a nominal voltage of approximately 3.7 V/cell, resulting in a nominal battery voltage of approximately 15 V. The battery 252 may be a so called "Smart Battery" meaning that many of its functions including how it is charged and discharged is controlled by one or more a microcontrollers connected to the cells within the housing of the battery 252 as described in the Smart Battery Data Specification, Revision 1.1, first published Dec. 11, 1998 by the Smart Battery System Implementers Forum (SBS-IF).

An integrated transducer and generator (TAG) component 256 houses both a generator and a transducer. Like the battery 252, the TAG 256 is removably connected to the ultrasonic surgical instrument 250. Thus, in some embodiments only the battery 252 and the TAG 256 are reusable and the remainder of the ultrasonic surgical device 250 (including cannula 120, waveguide 114, and end effector 117) is disposable. With respect to FIG. 2A, the generator portion of the TAG 256 takes DC energy from the battery 252 and converts it to AC (i.e., a sinusoidal form) and controls the converted energy to power the ultrasonic transducer portion of the TAG 256 and therewith drive the waveguide 114 formed within the cannula 120 and ultimately the blade 118, as described above with respect to FIG. 3, or as will be discussed in greater detail below with reference to FIG. 10.

The end effector is operated by an actuator mechanism 254. Pulling the actuator 254 in the direction of the battery 252 (i.e., proximally) causes the end effector 117 to close, for example to trap tissue in the end effector 117. After clamping tissue in the end effector 117, a user presses the trigger 258 to cause power to be delivered from the battery to the TAG 256 and start it oscillating. The TAG 256 transfers its oscillatory motion to the waveguide 114 housed in the cannula 120 to the blade 118, causing the blade 118 to vibrate near or at the resonant frequency of the ultrasonic surgical instrument 250 in order to cut, seal or coagulate tissue clamped in the end effector 117. The transducer portion of the TAG 256 in combination with the waveguide 114 and the blade 118 together form an oscillating structure.

Figures 4, 5:
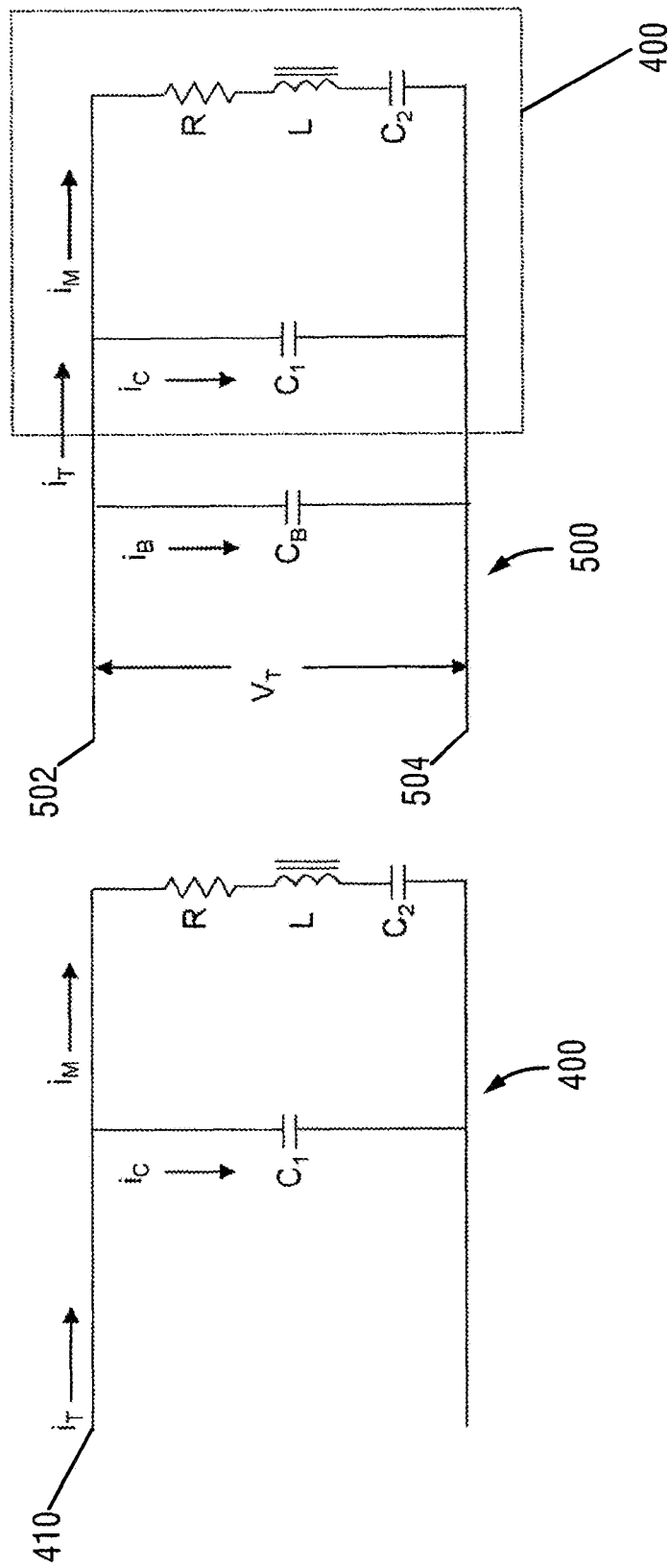
FIG. 4 is a circuit diagram of an elemental series circuit model for a transducer in accordance with an exemplary embodiment of the present disclosure.
FIG. 5 is a circuit diagram incorporating the transducer of FIG. 4 for monitoring a motional current of a transducer in accordance with an exemplary embodiment of the present disclosure.

FIG. 4 is a schematic circuit diagram of a model transducer 400, such as transducer 316 or the transducer portion of TAG 256, which contains piezo-electric material. Piezo-electric transducers are well known in the art. The mass and stiffness of the piezo-electric material creates a mechanically resonant structure within the transducer. Due to the piezo-electric affect, these mechanical properties manifest themselves as electrically equivalent properties. In other words, the electrical resonant frequency seen at the electrical terminals is equal to the mechanical resonant frequency. As shown in FIG. 4, the mechanical mass, stiffness, and damping of the transducer 316 may be represented by a series configuration of an inductor/coil L, a capacitor $C_2$, and a resistor R, all in parallel with another capacitor $C_1$. The electrical equivalent transducer model 400 is quite similar to the well-known model for a crystal.

Flowing into an input 410 of the electrical equivalent transducer model 400 is a transducer current $i_T$. A portion $i_C$ of $i_T$ flows across the parallel capacitor $C_1$, which for the majority of the expected frequency range, retains a substantially static capacitive value. The remainder of $i_T$, which is defined as $i_M$, is simply $(i_T-i_C)$ and is the actual working current. This remainder current $i_M$ is referred to herein as the "motional" current. That is, the motional current is that current actually performing the work to move the waveguide 320.

As discussed above, some known designs regulate and synchronize with the total current $i_T$, which includes $i_C$ and is not necessarily an indicator of the actual amount of current actually causing the motion of the waveguide 320 of the transducer 316. For instance, when the blade of a prior-art device moves from soft tissue, to more dense material, such as other tissue or bone, the resistance R increases greatly. This increase in resistance R causes less current $i_M$ to flow through the series configuration R-L-$C_2$, and more current $i_C$ to flow across capacitive element $C_1$. In such a case, the waveguide 320 slows down, degrading its performance. It may be understood by those skilled in the art that regulating the overall current is not an effective way to maintain a constant waveguide speed (i.e. vibrating at resonance). As such, one embodiment of the present disclosure monitors and regulates the motional current $i_M$ flowing through the transducer 316. By regulating the motional current $i_M$, the movement distance of the waveguide 320 can be regulated.

FIG. 5 is a schematic circuit diagram of an inventive circuit 500 useful for understanding how to obtain the motional current $i_M$ of a transducer 400. The circuit 500 has all of the circuit elements of the transducer 400 plus an additional bridging capacitive element $C_B$ in parallel with the transducer 400 of FIG. 4. However, the value of $C_B$ is selected so that $C_1/C_B$ is equal to a given ratio r. For efficiency, the chosen value for $C_B$ should be relatively low. This limits the current that is diverted from $i_M$. A variable power source $V_T$ is applied across the terminals 502 and 504 of the circuit 500, creating a current $i_B$ through the capacitive element $C_B$, a current $i_T$ flowing into the transducer 400, a current $i_C$ flowing through capacitor $C_1$, and, finally, the motional current $i_M$. It then follows that $i_M = i_T - r^* i_B$. This is because:

$$i_B = C_B \cdot \frac{\partial V_r}{\partial_t} = \frac{C_1}{r} \cdot \frac{\partial V_r}{\partial_t}$$

and $$i_c = C_i \cdot \frac{\partial V_T}{\partial_t}$$

Therefore, $i_C = r^* i_B$ and, substituting for $i_C$ in the equation $i_M = i_T - i_C$, leads to $$i_M = i_T - r^* i_B.$$

By knowing only the total current and measuring the current through the bridge capacitor $i_B$, variations of the transducer's motional current $i_M$ can be identified and regulated. The driver circuit 308, then, acts as a current controller and regulates the motional current $i_M$ by varying an output of the transformer 310 based on the product of the current flowing through the bridge capacitance $C_B$ multiplied by the ratio r subtracted from a total current $i_T$ flowing into the transducer 400. This regulation maintains a substantially constant rate of movement of the cutting blade 318 portion of the waveguide 320 across a variety of cutting loads. In one embodiment, the sensing circuits 314 measure the motional voltage and/or motional current. Current and voltage measuring devices and circuit configurations for creating voltage meters and current meters are well known in the art. Values of current and voltage can be determined by any way now known or later developed, without limitation.

Figure 6:
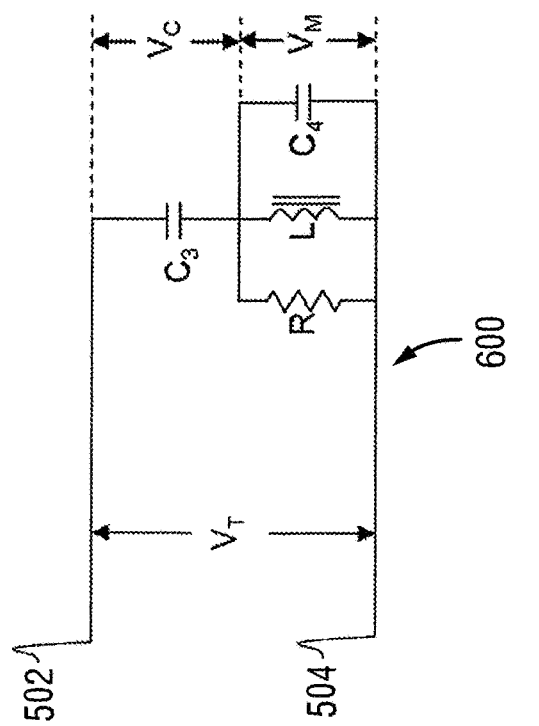
FIG. 6 is a circuit diagram of an elemental parallel circuit model of a transducer in accordance with an exemplary embodiment of the present disclosure.

FIG. 6 shows another embodiment of the present disclosure, where the transducer 316 is schematically represented as a parallel configuration of a resistive element R, an inductive element L, and a capacitive element $C_4$. An additional capacitive element $C_3$ is in a series configuration between an input 502 and the parallel configuration of the resistive element R, the inductive element L, and the capacitive element $C_4$. This parallel representation models the action of the transducer in the "antiresonant" mode of operation, which occurs at a slightly different frequency. A transducer voltage $V_T$ is applied between the input terminals 502, 504 of the transducer 316. The transducer voltage $V_T$ is split between a voltage $V_C$ across capacitive element $C_3$ and a motional voltage $V_M$ across the parallel configuration of the resistive element R, the inductive element L, and the capacitive element $C_4$. It is the motional voltage $V_M$ that performs the work and causes the waveguide 320 to move. Therefore, in this exemplary embodiment, it is the motional voltage that should be carefully regulated.

Figure 7:
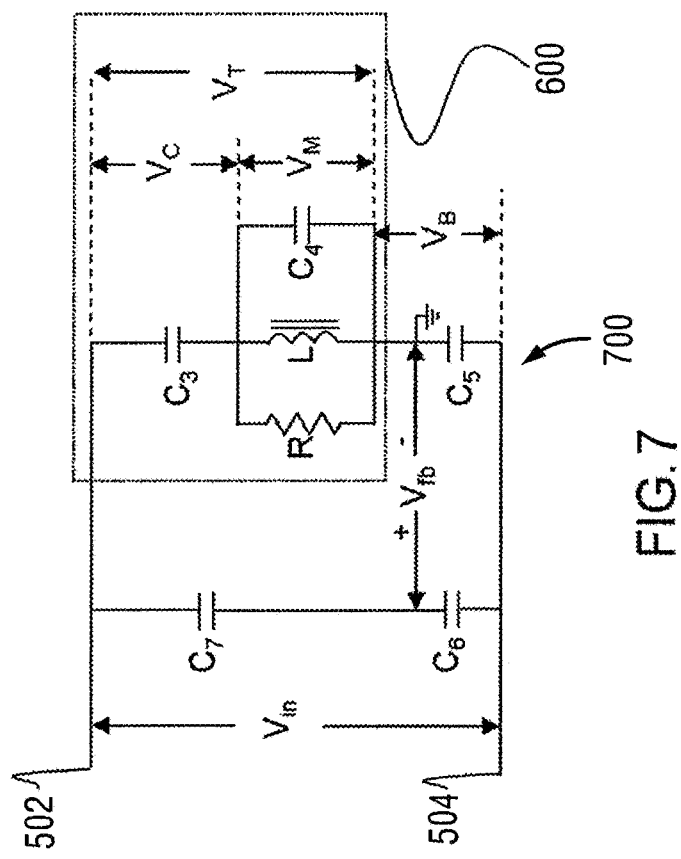
FIG. 7 is circuit diagram incorporating the transducer of FIG. 6 for monitoring the motional current of a transducer in accordance with an exemplary embodiment of the present disclosure.

FIG. 7 shows an exemplary embodiment of an inventive circuit configuration 700. The circuit configuration 1000 includes the transducer 600 of FIG. 6 and adds to it three additional capacitive elements $C_5$, $C_6$, and $C_7$. Capacitive element $C_5$ is in series with the transducer circuit 600 while the capacitive elements $C_6$ and $C_7$ are in series with one another and, together, are in parallel with the series combination of the capacitive element $C_5$ and the transducer circuit 600.

This circuit is analogous to a Wheatstone bridge measuring instrument. Wheatstone bridge circuits are used to measure an unknown electrical resistance by balancing two legs of a bridge circuit, one leg of which includes the unknown component. In the instant circuit configuration shown in FIG. 10, a motional voltage $V_M$, which equals $V_T - V_C$, is the unknown. By determining and regulating the motional voltage $V_M$, the configuration allows a consistent waveguide movement to be maintained as set forth below.

Advantageously, the capacitive element $C_7$ is selected so that its value is a ratio A of capacitive element $C_3$, with A being less than one. Likewise, the capacitive element $C_6$ is selected so that its value is the same ratio A of the capacitive element $C_5$. The ratio of $C_5/C_3$ is also the ratio A.

Because the ratio of $C_3/C_7$ is A and the ratio of $C_5/C_6$ is also A, the bridge is balanced. It then follows that the feedback voltage $V_{fb}$, divided by the motional voltage $V_M$, is also the ratio A. Therefore, $V_M$ can be represented as simply $A*V_{fb}$.

If the voltage across the transducer 600 is still $V_T$, an input voltage V in equals $V_T$ plus the voltage $V_B$ across the capacitive element $C_5$. The feedback voltage $V_{fb}$ is measured from a first point located between capacitive elements $C_6$ and $C_7$ and a second point located between the transducer and the capacitive element $C_5$. Now, the upstream components of the circuit 300 act as a voltage controller and vary the power $V_{in}$ to maintain a constant feedback voltage $V_{fb}$, resulting in a substantially constant motional voltage and maintaining a substantially constant rate of movement of the cutting blade 318 portion of the waveguide 320 across a variety of cutting loads. Again, the present disclosure is not simply regulating the input voltage $V_{in}$, it is varying the input voltage $V_{in}$, for the purpose of regulating the motional voltage $V_M$.

Figure 8:
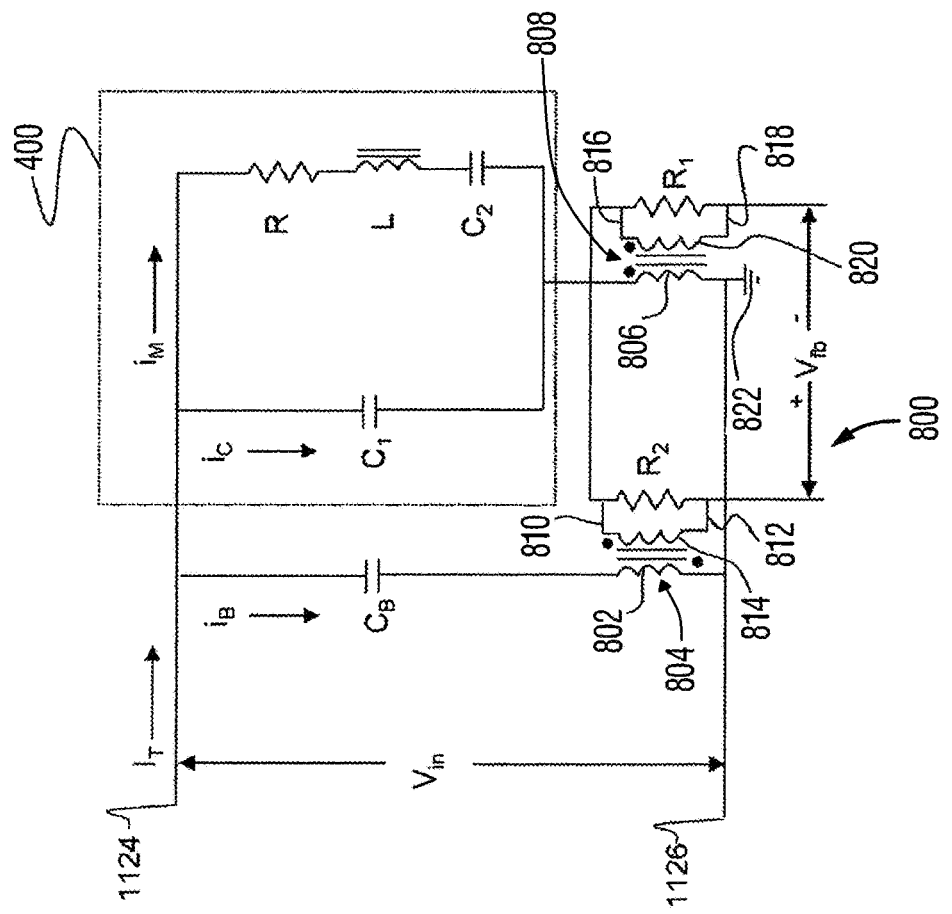
FIG. 8 is a circuit diagram incorporating the transducer of FIG. 4 for monitoring the motional current of a transducer in accordance with an exemplary embodiment of the present disclosure.

FIG. 8 shows another embodiment of the present disclosure where the transducer 400 is of the circuit configuration shown in FIG. 4. The configuration of FIG. 8 works similarly to that shown in FIG. 5 and as described above. However, in this circuit configuration 800, a pair of transformers 804 and 808 is used to determine and monitor the motional voltage $V_M$. In this embodiment, a primary winding 802 of the first transformer 804 is in a series configuration with a bridge capacitor $C_B$. Similarly, a primary winding 806 of the second transformer 808 is in a series configuration with the transducer 400. The leads 810 and 812 of the secondary winding 814 of the first transformer 804 are coupled through a resistor $R_2$. The leads 816 and 818 of the secondary winding 820 of the second transformer 808 are coupled through a resistor $R_1$. In addition, the first lead 810 of the secondary winding 814 of the first transformer 804 is directly connected to the first lead 86 of the secondary winding 820 of the second transformer 808.

Current $i_B$ passing through the primary winding 802 of the first transformer 804 induces a current in the secondary winding 814 of the first transformer 804. Similarly, the currents including $i_C$ passing through the capacitive element $C_1$ of the transducer 400 and the motional current $i_M$ of the transducer 400 combine and go through the primary winding 806 of the second transformer 808 to find ground 822. The current in the primary winding 806 induces a current on the secondary winding 820. As noted by the dots ("●") on the transformers 804, 808, the secondary windings 814 and 820 are in opposite directions from one another, with reference to the primary windings 802, 806, respectively, and induce a voltage $V_{fb}$ across resistors $R_1$ and $R_2$. By selecting values for $R_1$ and $R_2$ so that a ratio of $R_1/R_2$ is equal to the ratio of the values $C_B/C_1$, the feedback voltage $V_{fb}$ will always be proportional to the motional current $i_M$. Now, the upstream components of the circuit 300 (see FIG. 3) act as a voltage controller and vary the input power ($V_{in}$ and $I_T$) to maintain a constant feedback voltage $V_{fb}$, resulting in a substantially constant motional current $i_M$ and maintaining a substantially constant rate of movement of the cutting blade portion of the waveguide 320 across a variety of cutting loads. Again, this embodiment is not simply regulating the input voltage $V_{in}$, it is varying the input current $I_T$ for the purpose of regulating the motional current $i_M$.

Figure 9:
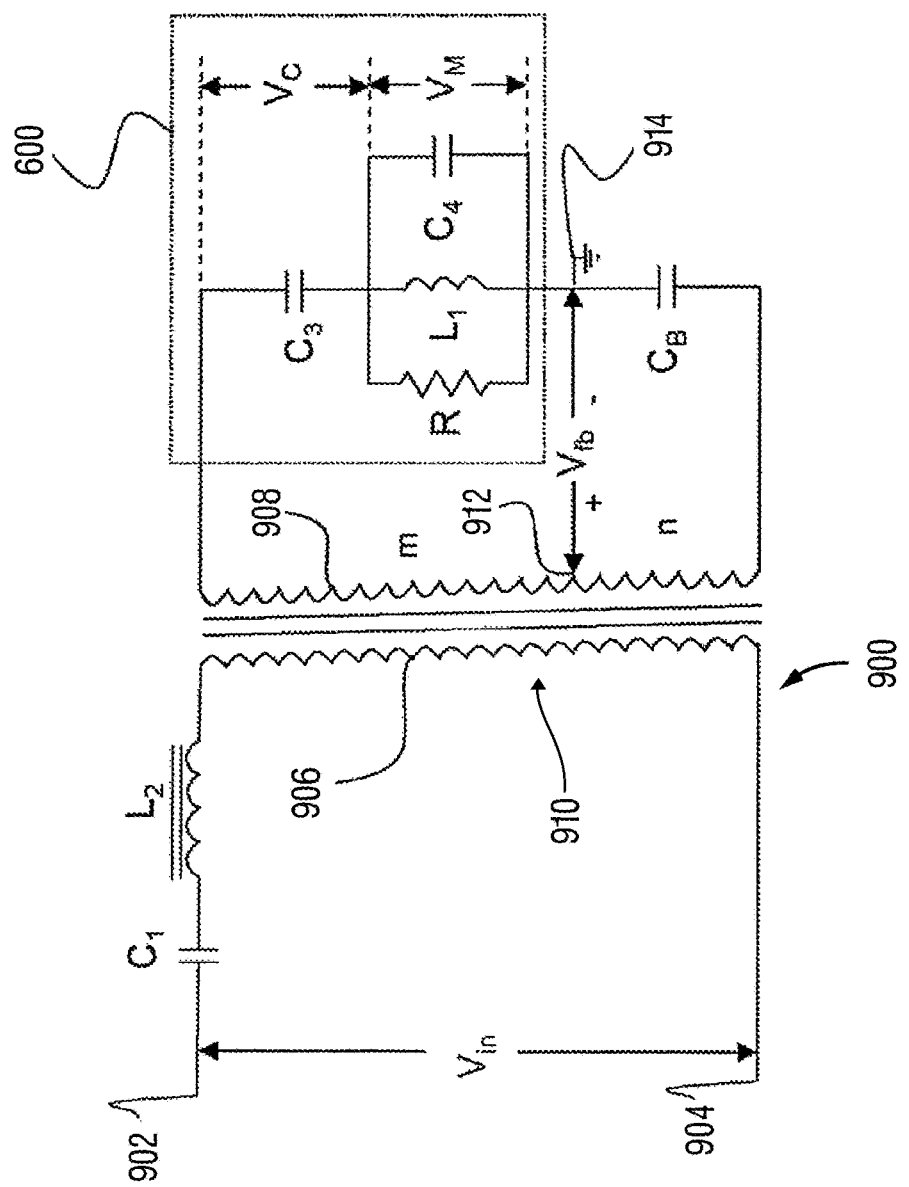
FIG. 9 is a circuit diagram incorporating the transducer of FIG. 6 for monitoring the motional current of a transducer in accordance with an exemplary embodiment of the present disclosure.

FIG. 9 shows another embodiment of the present disclosure where the transducer 600 is modeled by the circuit configuration shown in FIG. 6. In the configuration 900 of FIG. 9, a transformer 910 is used to determine and monitor the motional voltage $V_M$ of the transducer 600. In this embodiment, a primary winding 906 of the transformer 910 is in a series circuit configuration with an inductive element $L_2$ and a capacitive element $C_1$. A voltage $V_{in}$ is applied across input leads 902 and 904 of the circuit formed by the primary winding 906 of the transformer 910, the inductive element $L_2$, and the capacitive element $C_1$. A current through the primary winding 906 induces a corresponding current in the secondary winding 908 of the transformer 910. The secondary winding 908 of the transformer 910 is in a parallel configuration with a combination of the transducer 600 and a bridge capacitor $C_B$. The two components forming the combination are in a series configuration.

In this embodiment, the secondary winding 908 is tapped at a point 912. By tapping the secondary winding 908 at a point where a first portion of the secondary winding 908 has "m" turns and a second portion of the secondary winding 1208 has "n" turns (where n is less than m), a selectable percentage of the induced voltage on the secondary winding 908 appears from point 912 to ground 914.

Again, this circuit is analogous to a Wheatstone bridge measuring instrument. One leg is the first secondary winding "m," the second leg is the second secondary winding "n," the third leg is the transducer 600, and the fourth leg is the capacitor $C_B$. In the instant circuit configuration shown in FIG. 9, the voltage $V_M$ is the unknown. By determining and regulating the motional voltage $V_M$, a consistent waveguide movement is maintained.

By selecting a value of the bridge capacitor $C_B$ to be less than the transducer capacitance $C_3$ by the same percentage that the number of turns "n" is less than the number of turns "m" (i.e., min=$C_3/C_B$), the value of a feedback voltage $V_{fb}$ will reflect the motional voltage $V_M$. The disclosure can determine whether the motional voltage $V_M$ is changing by monitoring the feedback voltage $V_{fb}$ for changes.

By using the equivalent-circuit transducer model 600, which models a parallel-resonant (or "anti-resonant") transducer, the transducer may be driven in the parallel resonant mode of operation, where motion is proportional to voltage. The advantage of this mode of operation is that the required constant-voltage-mode power supply is simpler to design and safer to operate than a constant-current-mode power supply. Also, because the transducer has a higher impedance when unloaded (rather than a lower impedance when unloaded in the series-resonant mode of operation), it naturally tends to draw less power when unloaded. The parallel-resonant mode of operation, however, is more difficult to maintain because the resonant bandwidth is narrower than that of the series-resonant mode and it has a slightly different natural resonant frequency, hence, the mechanical components of the device must be specifically configured to operate at either the series resonant or parallel-resonant mode of operation.

Now, the upstream components of the circuit 300 act as a voltage controller and vary the power $V_{in}$ to maintain a constant feedback voltage $V_{fb}$, resulting in a substantially constant motional voltage $V_M$ and maintaining a substantially constant rate of movement of the cutting blade 318 portion of the waveguide 320 across a variety of cutting loads. Again, the present disclosure is not simply regulating the input voltage $V_{in}$, it is varying the input voltage $V_{in}$ for the purpose of regulating the motional voltage $V_M$.

Figure 10:
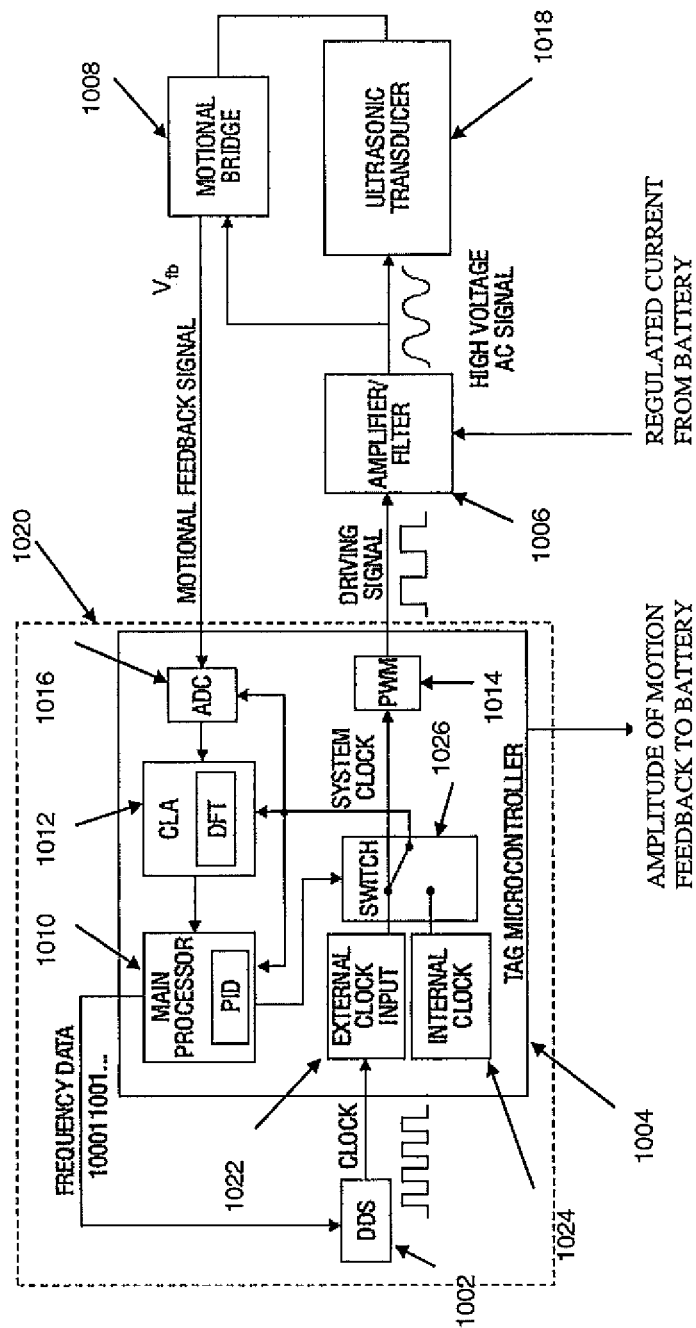
FIG. 10 is a diagrammatic illustration of the components of an ultrasonic surgical system of FIG. 2A having integrated power, control, drive and matching components in block diagram form in accordance with an exemplary embodiment of the present disclosure.

FIG. 10 depicts a control system 1000 that may be particularly useful when employed in an untethered ultrasonic surgical device 250 as shown in FIG. 2A, however, it may also be employed in more traditional corded devices as shown in FIGS. 1 and 2. As shown in FIG. 10, in addition to a transducer 1018 the TAG 256 (of FIG. 2A) includes a Direct Digital Synthesis ("DDS") 1002 integrated circuit, the TAG microcontroller 1004, an amplifier/filter circuit 1006, and a motional bridge 1008. The TAG microcontroller 1004 includes a main processor 1010, a control law accelerator 1012 ("CLA"), a pulse width modulator 1014 ("PWM"), and an analog-to-digital converter 1016 ("ADC"). The TAG microcontroller 1004 controls the frequency of the high voltage AC signal applied to the ultrasonic transducer 1018 to cause the ultrasonic transducer 1018 to vibrate at its resonant frequency. The TAG microcontroller 1004 controls the frequency of the high voltage AC signal using a phase lock loop 1020 (PLL) that is implemented by the DDS 1002, main processor 1010, CLA 1012, and the PWM 1014.

During normal operation, the PLL 1020 adjusts the frequency of the drive signal based on the phase of the motional feedback signal $V_{fb}$. To adjust the frequency of the drive signal, the main processor 1010 executes a PID control algorithm to determine frequency data based on the phase of the motional feedback signal $V_{fb}$. The main processor 1010 transmits the frequency data to the DDS 1002, which generates a clock signal having a frequency defined by the frequency data. The PWM 1014 receives the clock signal and generates a drive signal having a frequency that is in a predetermined and fixed relationship with the frequency of the clock signal generated by the DDS 1002. As will be understood by those of skill in the relevant art, at resonance, the drive signal is in phase with the motional feedback signal $V_{fb}$.

An Amplifier/Filter circuit 1006 combines the drive signal with the regulated current from the battery 252 to produce a high voltage AC signal having a frequency equal to the frequency of the drive signal. The high voltage AC signal is then applied to the ultrasonic transducer 1018. A motional bridge 1008 measures the mechanical motion of the ultrasonic transducer 1018 and provides a motional feedback signal representing the mechanical motion of the ultrasonic transducer. The ADC 1016 samples the motional feedback signal and the CLA performs a Discrete Fourier Transform (DFT) on the sampled motional feedback signal to obtain phase information of the motional feedback signal with reference to the drive signal. Using the motional feedback $V_{fb}$, the PLL 1020 adjusts the frequency of the drive signal based on the phase of the motional feedback signal to achieve and maintain resonance of the ultrasonic transducer.

The TAG microcontroller 1004 includes an external clock input 1022 which enables the DDS 1002 to input the clock signal it generates into the microcontroller 1004. The TAG microcontroller 1004 also includes an internal clock 1024, and a switch 1026 that switches the system clock between the external clock input 1022 and the internal clock 1024. As shown in FIG. 10, the system clock drives the main processor 1010, the CLA 1012, and the ADC 1016. During startup, the internal clock 1024 generates the system clock signal. After the DDS 1002 starts generating a clock signal, the TAG microcontroller switches the system clock from the internal clock 1024 to the clock signal generated by the DDS 1002 and fed to the external clock input 1022.

In each of the circuit configurations described and shown in FIGS. 4-9, circuit component degradation can impact negatively the entire circuit's performance. One factor that directly affects component performance is heat. For this reason, the circuit depicted in FIG. 3 includes a sensing circuit 314 which senses the temperature of the transformer 310. This temperature sensing is advantageous as transformer 310 may be run at or very close to its maximum temperature during use of the device. Additional heat will cause the core material, e.g., the ferrite, to break down and permanent damage can occur. If a predetermined maximum temperature is reached the circuit 300 can, for example, reduce the driving power in the transformer 310, signal the user, turn the power off completely, pulse the power, or engage in other appropriate responses.

Referring back to FIG. 1, in one embodiment, the processor 302 is communicatively coupled to the end effector 117, which is used to place material in physical contact with the blade 118. The end effector 117 has a range of clamping force values and the processor 302 (FIG. 3) varies the motional voltage $V_M$ based upon the received clamping force value. Because high force values combined with a set motional rate can result in high blade temperatures, a temperature sensor 322 can be communicatively coupled to the processor 302, where the processor 302 is operable to receive and interpret a signal indicating a current temperature of the blade 318 from the temperature sensor 322 and determine a target frequency of blade movement based upon the received temperature.

According to an embodiment of the present disclosure, the PLL (308 or 1020), is able to determine a frequency of transducer 316, 1018. The known resonant frequency of the transducer 316, 1018 (and therewith the resonant frequency of the waveguide and blade) at any particular time can be utilized for purposes beyond merely tuning and maintaining the operation of the device at resonance. One such purpose is for detecting temperature of the blade 118.

Figure 11:
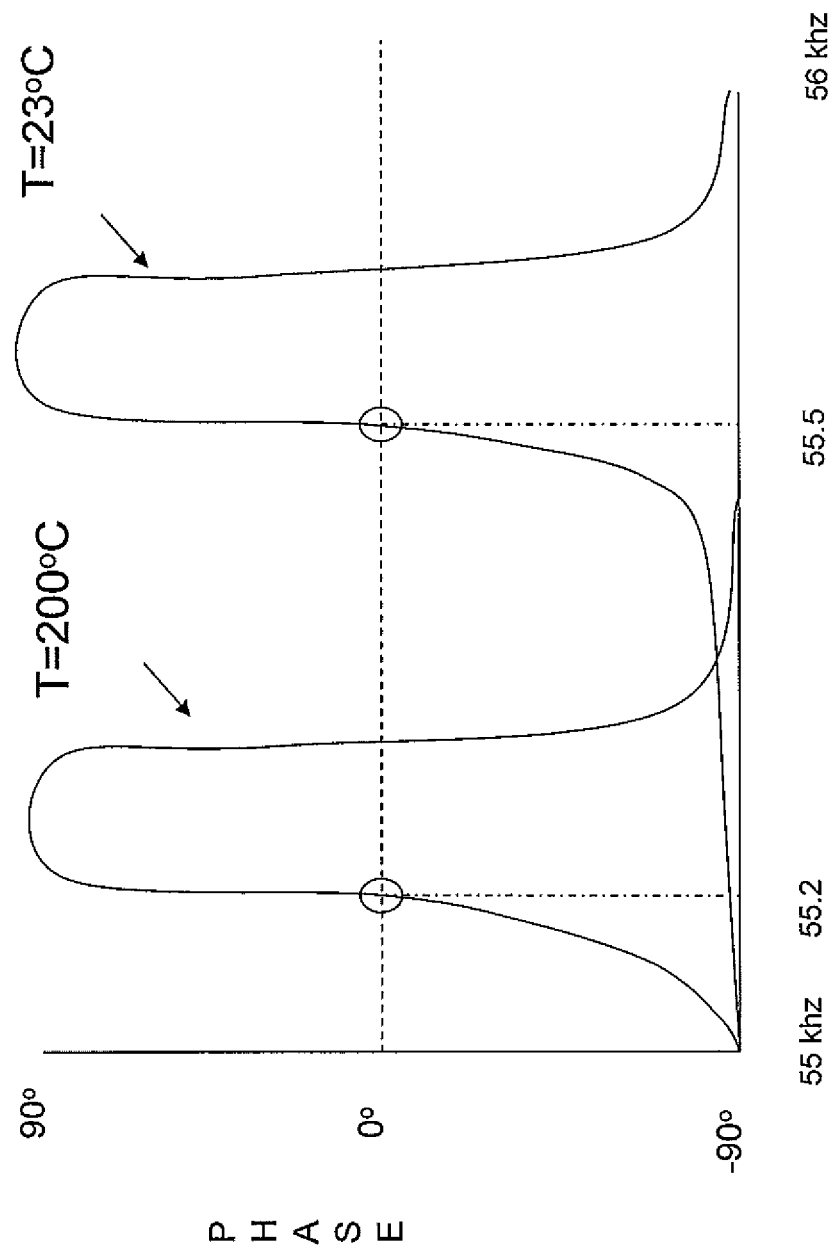
FIG. 11 is a Bode plot of the frequency response of an ultrasonic surgical instrument associated with heating as compared to phase in accordance with an exemplary embodiment of the present disclosure.
Figure 12:
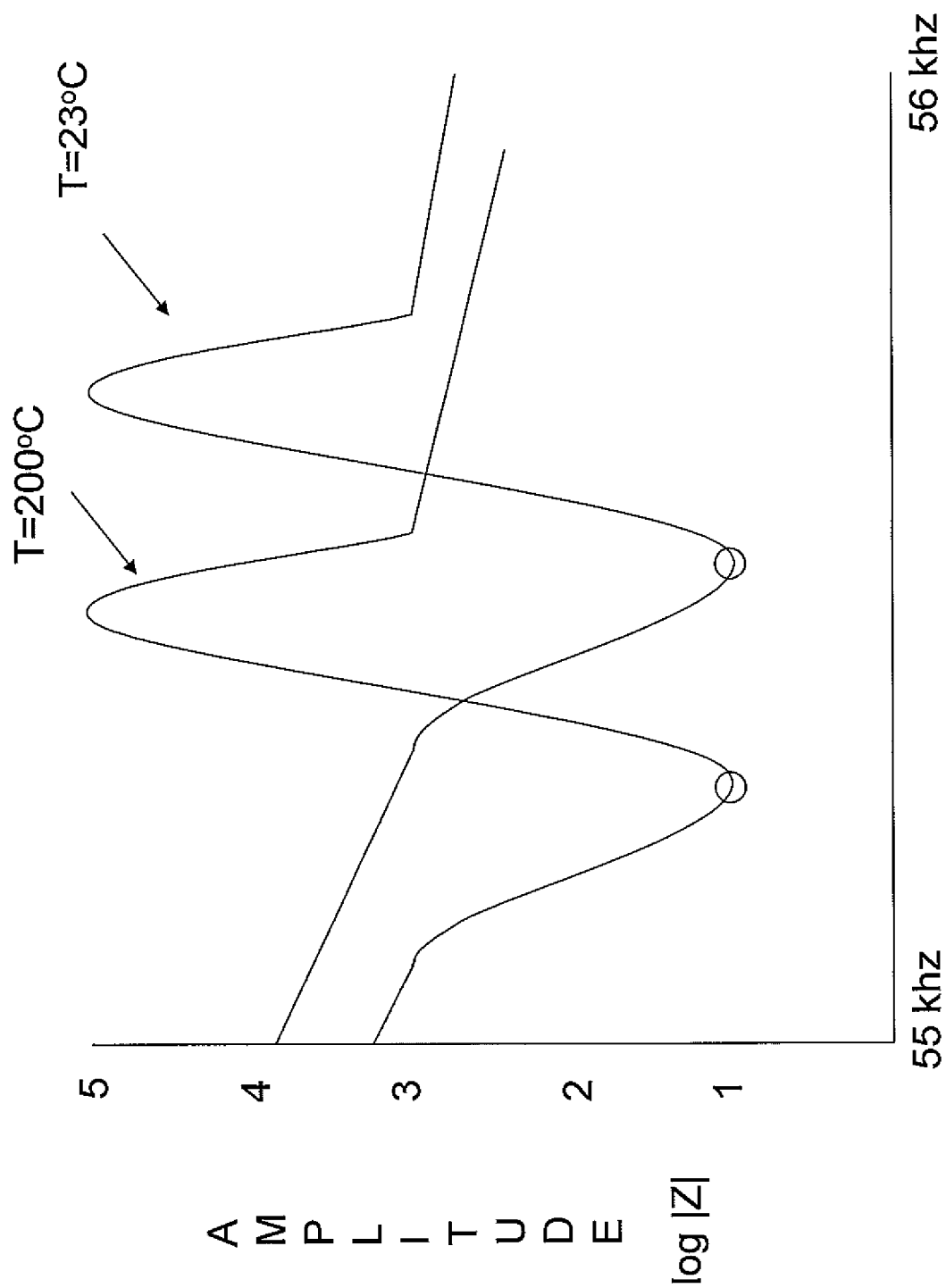
FIG. 12 is a Bode plot of the frequency response of an ultrasonic surgical instrument associated with heating as compared to impedance in accordance with an exemplary embodiment of the present disclosure.

FIGS. 11 and 12 are Bode plots of an ultrasonic surgical instrument, according to any of the embodiments of the present disclosure. As noted above, during use of an ultrasonic surgical instrument heat is generated. The resonant frequency of a harmonic system depends on a variety of factors including material density, material bulk or Young's modulus, the speed of sound, the diameter of the components, and other factors. Many of these factors are temperature dependent and can vary significantly when the system is heated. The composite result of these changing factors is observable by monitoring the resonant frequency of the system as it heats, for example during use of an ultrasonic surgical instrument.

FIG. 11 depicts the frequency response caused by the generation of heat on the resonant frequency of the oscillating structure (i.e. transducer 1018, waveguide 114, and blade 118). At room temperatures, for example 23° C., one desirable resonant frequency for the system may be about 55.5 kHz. This is noted on the plot in FIG. 11 at the zero crossing indicating 0° of phase shift from the drive signal. As can be seen in the plot of FIG. 11, when the temperature of the system increases, as is expected during operation, the resonant frequency shifts. Specifically, as shown in FIG. 11, when the resonant frequency drops approximately 300 Hz from 55.5 kHz to 55.2 kHz a temperature increase from 23° C. to 200° C. is observed. A similar shift in frequency is observable in the plot of FIG. 12, where the amplitude of the impedance Z of the system is monitored. Again the minimum impedance amplitude Z, which indicates that the system is operating at resonance, shifts from approximately 55.5 kHz to approximately 55.2 kHz.

By monitoring the change in resonant frequency of the system plotted against phase or impedance amplitude, the temperature of the system can then be estimated. For example, as shown in FIG. 11 a frequency shift of 300 Hz for that system represents a change in temperature from about 23° C. to about 200° C. Thus, by observing the resonant frequency of the system at room temperature and then tracking the resonant frequency of the system as it's used, the temperature of the oscillating structure can be estimated. This can then be accomplished without any separate element specifically intended for temperature sensing, but rather just by monitoring the system feedback during use. As noted above, with respect to FIGS. 4-9 the resonant frequency can be determined monitoring $V_{fb}$ which is representative of the motional voltage, and can be compared to the drive signal to ascertain phase and frequency information. However, it is also possible to monitor the impedance, as plotted in FIG. 12 to derive the resonant frequency information without departing from the scope of the present disclosure.

In one embodiment of the present disclosure, the ultrasonic surgical instrument 250 is tested for its room temperature resonance frequency during manufacture and this value is stored in a memory accessible by the microprocessor or microcontroller. Once the ultrasonic surgical instrument is put into use, i.e., the transducer is energized and begins to oscillate, the resonance frequency of the ultrasonic surgical instrument 250 is measured periodically, for example every 5 ms. Based on the instantaneous resonant frequency, a calculation can be performed to determine the temperature of the oscillating structure (i.e., transducer 1018, waveguide 114, and blade 118).

Alternatively, because most ultrasonic surgical instruments 250 employ one or more replaceable components, part of the start-up routine of the ultrasonic surgical instrument 250 could include a brief energization to determine its resonant frequency as assembled by the physician. For example, in the device shown in FIG. 2A both the TAG 256 and the battery 252 are reusable, while the remainder of the ultrasonic surgical instrument 250, including the cannula 120, waveguide 114, and blade 118, are disposable components. Thus, in such a device it is impractical to measure the resonant frequency of the system until the disposable portion is connected to the system, particularly the TAG 256. Accordingly, a test to determine the resonant frequency of the assembled device could be undertaken prior to its first use of the ultrasonic surgical instrument 250. This test may be user initiated, or could be automatically run upon assembly of the device as part of the surgical instrument's test routine before allowing use. The resonant frequency as determined by the test should be stored in the memory of the ultrasonic surgical instrument 250. The stored room temperature resonant frequency may be set each time the ultrasonic surgical instrument is assembled, thus each time the TAG 256 is mated with a new disposable portion of the ultrasonic surgical instrument 250, the routine is performed and the new resonant frequency overwrites any existing resonant frequency data already stored in memory.

Alternatively, though likely to incur some loss in accuracy, the resonant frequency could be stored in a memory in the TAG 256 upon the TAG's first assembly with the battery 252 and a disposable portion to form the ultrasonic surgical instrument 250. This one time determined resonant frequency could then be used as the basis for all future resonant frequency comparisons to determine the temperature of an ultrasonic surgical instrument 250 into which that TAG 256 has been connected.

Figure 13:
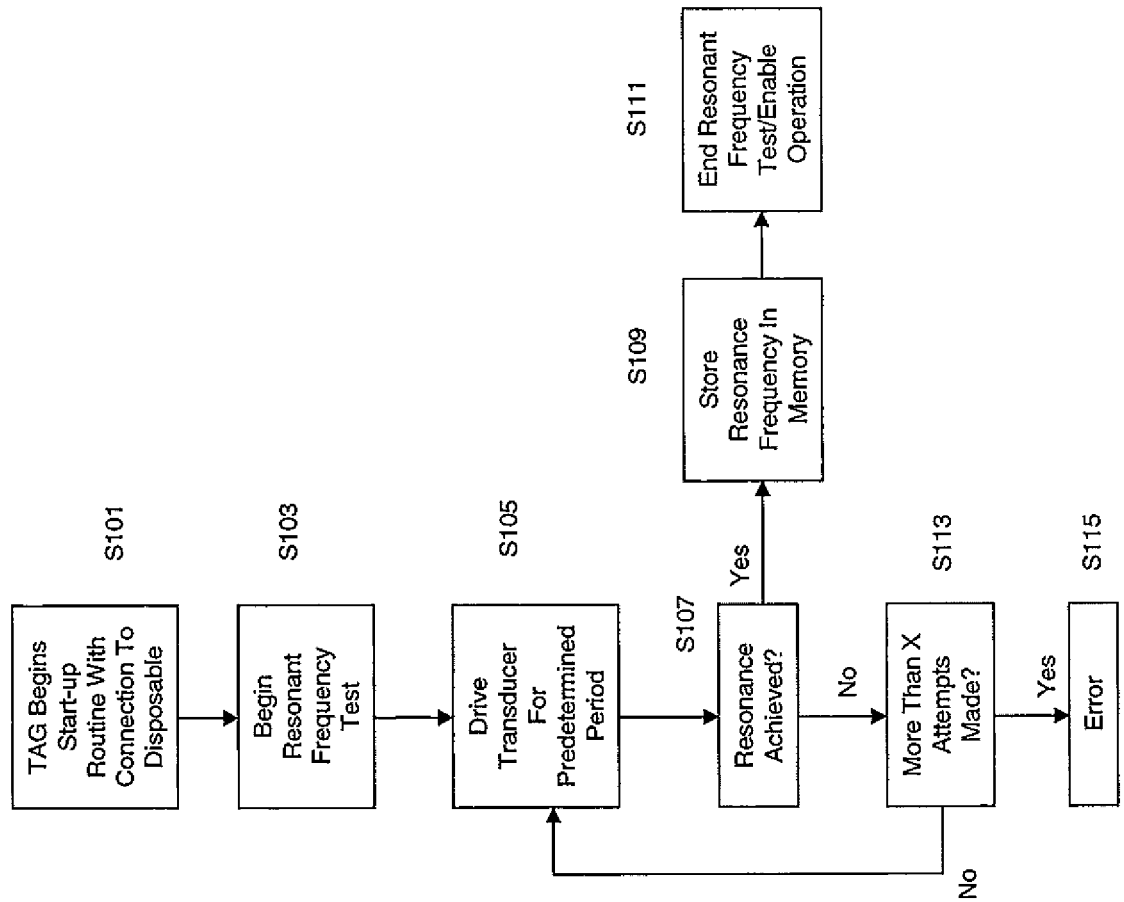
FIG. 13 is a simplified start-up routine for acquiring a resonant frequency of an ultrasonic surgical instrument in accordance with an exemplary embodiment of the present disclosure.

FIG. 13 is a simplified flow chart depicting a computer program storable in the memory of an ultrasonic surgical device of a start-up routine for determining a room temperature resonant frequency for an ultrasonic surgical instrument, such as that depicted in FIG. 2A. Once the TAG 256 is connected to the remainder of the ultrasonic surgical instrument 250, and the battery 252 is connected, a start-up routine is enabled at step S101. As part of the start-up routine the resonant frequency test is begun at S103. The transducer is driven for a predetermined period of time at S105. The period of time the transducer is driven should be sufficient to determine the resonant frequency of the ultrasonic surgical instrument 250 at room temperature as assembled S107. If the resonance frequency is determined, that frequency is stored in memory S109 and the resonant frequency test is ended S111 and the ultrasonic surgical device 250 is enabled for operation. If resonance is not achieved, the routine at step S113 may check to determine how many attempts at achieving resonance have been undertaken, for example five attempts may be permitted. If more than five attempts have been made without achieving resonance then an error is signaled at S115. If the number of available attempts has not exceeded the maximum then the routine loops back to step S105 and attempts to achieve resonance again until either resonance is achieved and the frequency value can be stored in memory of the available attempts is exceeded and an error is produced.

Figure 14:
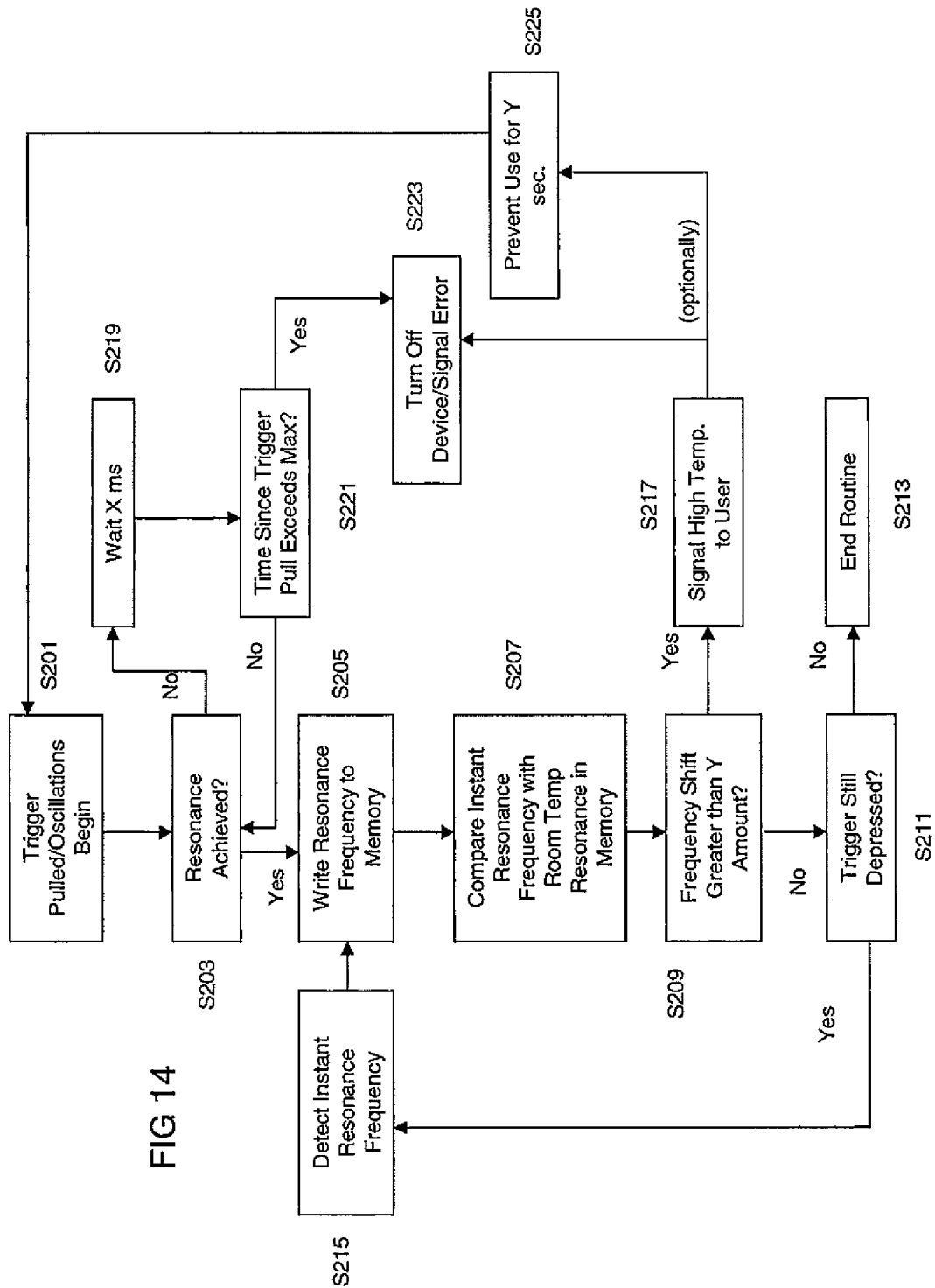
FIG. 14 is a flow diagram of a system for detecting the temperature of an ultrasonic surgical instrument as a function of frequency response in accordance with an exemplary embodiment of the present disclosure.

FIG. 14 is a simplified flow chart depicting a computer program storable in the memory of an ultrasonic surgical device for determining the temperature of the system (transducer, waveguide, and blade). Those of skill in the art will recognize that this process may be employed regardless of how that initial room temperature resonant frequency is determined, whether it is written into memory during manufacture of the TAG 256, determined at the first use of the TAG 256, or determined anew each time the TAG 256 is connected to the remainder of the ultrasonic surgical device 250.

In FIG. 14, the trigger 258 of the ultrasonic surgical instrument 250 is pulled in step S201. Next a check of resonance is undertaken at step S203. One of skill in the art will understand that it may be desirable to insert a delay between steps S201 and S203 to allow the ultrasonic surgical device 250 opportunity to achieve resonance. If resonance is achieved, the value of the frequency at resonance is written to memory in the device at step S205. Next a comparison is made of the instant resonant frequency to the room temperature resonant frequency at step S207. If the frequency shift or response is less than a predetermined amount Y in step S209, the routine looks to see if the trigger is still depressed in step S211. If the trigger is no longer depressed the routine is ended at step S213. If, however, the trigger is still depressed a new instant resonance frequency is detected at step S215. The detection step in S215 may be following a set delay. The newly detected resonance frequency is then written to memory in step S205. In some embodiments only one value of instant resonance frequency is retained in memory to compare with the room temperature resonance frequency. In other embodiments a log of resonance frequencies can be stored in memory. This historical record may be useful in reviewing historical use of a device in the event of a failure or other incident requiring analysis of device use.

At step 209, if the frequency shift is greater than a predetermined amount, for example 300 Hz, then a signal may be sent to the user to indicate that the ultrasonic surgical device 250 is estimated to be above a certain temperature, for example 200° C. The alert to the user may be an audible tone, a light indicator such as an LED on the device, or a tactile response that is felt by the user in the handle of the ultrasonic surgical instrument 250.

Optionally, the ultrasonic surgical instrument may automatically switch off at step S223 based on achieving this temperature or an interlock S225 may prevent energization of the ultrasonic surgical instrument for a period of time (Y see), for example 15 seconds to allow the ultrasonic surgical device 250, and particularly the blade 118 to cool, after which period the trigger 258 may be re-pulled at step S201.

Similarly, at step S203 if resonance has not yet been achieved, a delay X (for example 5 ms) is triggered at step S219, after which at step S221 an inquiry is made to determine whether too much time has passed since the initial trigger 258 pull and achieving resonance. If too much time has passed then the device may be turned off and an error signaled at step S223.

Those of skill in the art will recognize that in addition to having a single frequency shift at which a high temperature signal is generated, the memory may store a series of frequency shifts and can generate a progressive signal of temperature to the user. For example, if the frequency shift is 100 Hz the device may generate a green visual signal to indicate that the temperature increase is not great, perhaps only to 70° C. Similarly, a yellow visual signal could be used to indicate a 200 Hz resonant frequency shift, indicative of perhaps a temperature of 130° C.

Alternatively, an empirical formula may be employed and stored in memory of the ultrasonic surgical device for converting a sensed frequency response into an estimated temperature. Thus, when the instantaneous resonant frequency is detected, the formula, which may include the room temperature resonant frequency and/or a weighted frequency response to temperature comparison function, is utilized to estimate a temperature change equivalent to the frequency response. This can again be tied to visual, audible or other signaling means. In such a situation it would be possible to present the estimated temperature value to the user via a display or, for example, a liquid-crystal display (LCD).

An exemplary formula is:

$$T_{Est} = T_{Room} + \frac{(F_{Room} - F_{Inst.}) \cdot 180 \ C.}{300 \ Hz}$$

where T is temperature, F is frequency, and Room represents the values measured at start-up, and Inst. is the instantaneous measurement. Thus by using the instantaneous frequency of the blade and calculating an estimated temperature the ultrasonic surgical instrument can be controlled by the microcontroller in the generator to warn the surgeon that the tip is warm or hot, as described above.

Figure 15:
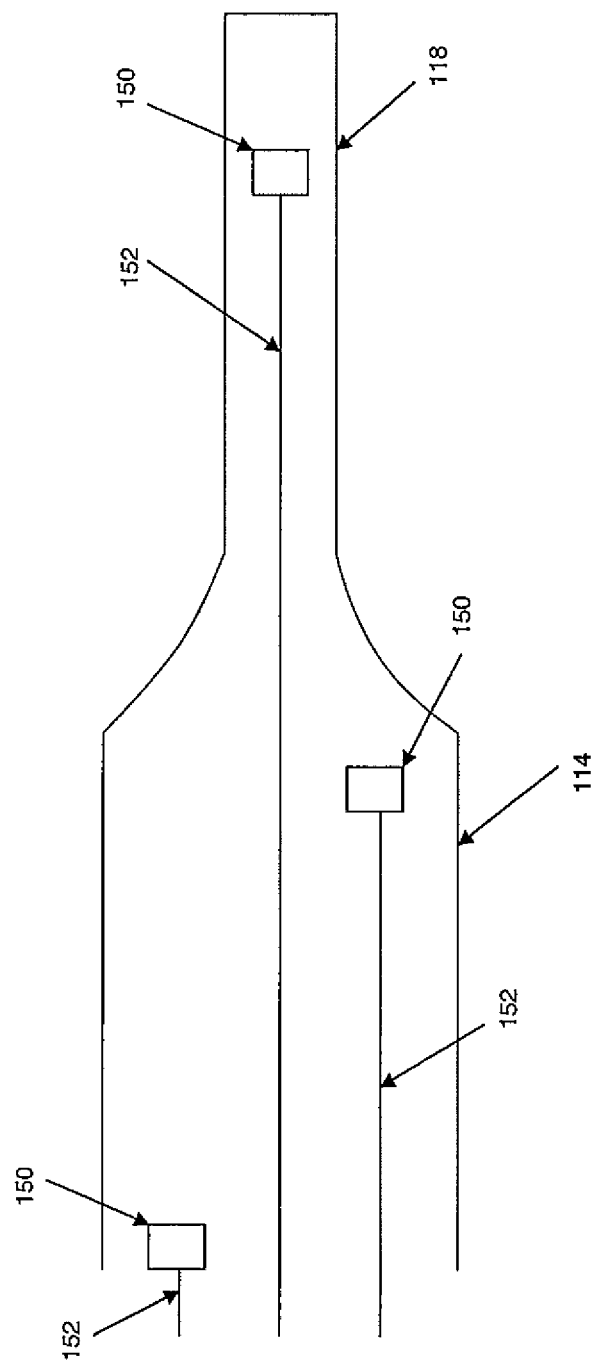
FIG. 15 is an enlarged profile view of a portion of a wave guide and a blade of an ultrasonic surgical instrument including resonators in accordance with an exemplary embodiment of the present disclosure.

FIG. 15 depicts an enlarged view of a blade 118 and the distal end of the waveguide 114 of the ultrasonic surgical instruments shown in FIGS. 1, 2 and 2A. Imbedded within the blade 118 is an ultrasonic resonator 150. The ultrasonic resonator 150 may be formed of a piezo-electric crystal of the type described above, however, rather than taking electrical energy and converting it to mechanical motion, the resonator 150 (e.g., an accelerometer), takes the applied mechanical force and converts it to an electrical signal that is sent to the microprocessor 302 or microcontroller 1004 via lead 152 for analysis.

In one embodiment an ultrasonic resonator 150 is placed in the blade 118 of the ultrasonic surgical instrument 250. The ultrasonic resonator 150 is sized such that it has a resonant frequency far removed from that of the ultrasonic surgical instrument 256 (e.g., TAG 256, waveguide 114, and blade 118). For example, if the ultrasonic surgical instrument 250 has a room temperature resonant frequency of 55.5 kHz, and the ultrasonic resonator 150 may have a room temperature resonant frequency of 101.7 kHz or about 100 kHz. However, the resonant frequency of the resonator 150 may be even further removed from that of the ultrasonic surgical instrument 250, it may be for example 800 kHz or other frequencies outside the operating range of the ultrasonic surgical instrument 250.

In operation, the mechanical motion of the blade 118 imparts mechanical force on the ultrasonic resonator 150. This mechanical motion is converted by the resonator 150 into an electrical signal. The greater the mechanical force the greater the electrical signal that is produced. As a result of the electrical signal being dependent upon the force applied, the greatest electrical signal will be generated at anti-nodes of the ultrasonic surgical instrument 250, where the amplitude of the harmonic oscillation is greatest. As explained above the blade 118 is most effectively located at an antinode so that the maximum amplitude of mechanical motion can be imparted on the tissue. Thus, though a resonator 150 can be located at any location along waveguide 114 and blade 118, it is more effective to place them in proximity of the anti-nodes, or at least removed from the nodes which have little to no movement.

When the blade 118 heats up during use the resonator 150 will also heat up. This heating of the resonator 150 will have an effect on electrical signal generated. As the blade 118 is heated its resonant frequency shifts, so too the resonant frequency of the resonator 150 shifts and therewith the components of the electrical signal (e.g., frequency and voltage) generated by the resonator 150 and transmitted to the microprocessor 302 or microcontroller 1004. Because the resonator 150 is reasonably isolated from the other components of the ultrasonic surgical device 250, the primary cause of the change in resonant frequency and therewith the electrical signal generated by the resonator is the increase in temperature caused by the heating of the blade 118.

As with the monitoring of the resonant frequency described above with respect to FIGS. 11-14, the resonant frequency of the resonator 150 may be stored in the memory of the ultrasonic surgical device 250 during manufacture. Similarly, during start-up the properties of the electrical signal (e.g., frequency and voltage) produced by the resonator 150 when the ultrasonic surgical device 250 achieves resonance at room temperature may be determined and stored in memory. The electrical signal produced by the resonator 150 at room temperature resonance may then be compared to the electrical signal produced by the resonator 150 as the resonant frequency of the ultrasonic surgical device 250 shifts during use due to its heating. By comparing the room temperature electrical signal values with values sensed during operation, the temperature of the resonator 150 at any point in time may be determined either through the use of an empirical formula, by using a look-up table, as described herein with respect to detecting the temperature of the entire oscillatory structure with reference to FIG. 14, or by other means known to those of skill in the art.

By placing multiple resonators 150 along the waveguide 114 and blade 118, it is possible to determine which components of the ultrasonic surgical instrument 250 are heating and to what extent they are heating by comparing the signals produced by each of the resonators 150. In this way the ultrasonic surgical instrument 250, and particularly the microprocessor 302 or 1004, can discern that though there has been a frequency shift of 300 Hz of the entire ultrasonic system (e.g., TAG 256, waveguide 114, and blade 118) because only the electrical signal generated by the resonator 150 located in the blade 118, for example, has changed as compared to its electrical signal produced as room temperature resonance, it is only the blade 118 that has undergone significant heating. Thus multiple resonators 150 allows for a temperature gradient along the oscillating structure to be ascertained. Alternatively, if resonators 150 on both the blade 118 and the waveguide 118 show a change in electrical signal, the ultrasonic surgical instrument 250 can determine that most if not all of the oscillating structure has experienced heating.

In an alternative embodiment, the resonators 150 are driven by a separate signal generator. Thus for example, a drive signal at 101.7 kHz is applied to the one or more resonators 150 and the return signal of each resonator is monitored to maintain oscillation of the resonators 150 at resonance. As the individual components of the ultrasonic surgical instrument 250 heat up, the resonant frequency of each resonator 150 will change independent of the temperature of that specific resonator 150. The frequency shift of each individual resonator 150 can be compared to the original 101.7 kHz to determine the temperature of each resonator in the same manner as described above with respect to detection of the temperature of the overall system in FIGS. 13 and 14. In this manner, additional information can be provided to the user such that the surgeon is signaled when only a single component is achieving high temperatures (e.g., the blade 118), or whether the entire system (e.g., TAG 256, waveguide 114 and blade 118) is heating.

As with the implementation described above with respect to FIGS. 13 and 14, various indicators can be provided to the user including visual and audible, as well as interlocks that prevent the use of the ultrasonic surgical instrument 250 for a predetermined time, or until the sensed temperature of the component or system has returned to an acceptable level.

Alternatively, the resonators 150 could be simple metal protrusions (not shown) extending from the blade 118. Each metal protrusion has a specific resonant frequency different from the rest of the blade 118. The resonant frequency of the protrusion will depend upon the mass, length, material and other factors known to those of skill in the art. Using a Fourier Transform, either a DFT as described above or a Fast Fourier Transform, focus on the known peaks of the resonators 150 (i.e., their resonant frequency) can be undertaken, much in the way that the resonant frequency of the blade is considered. By focusing on changes at or around the resonant frequencies of the resonators 150, changes in temperature of the resonators 150 can be determined in much the same way as described above.

Figure 16:
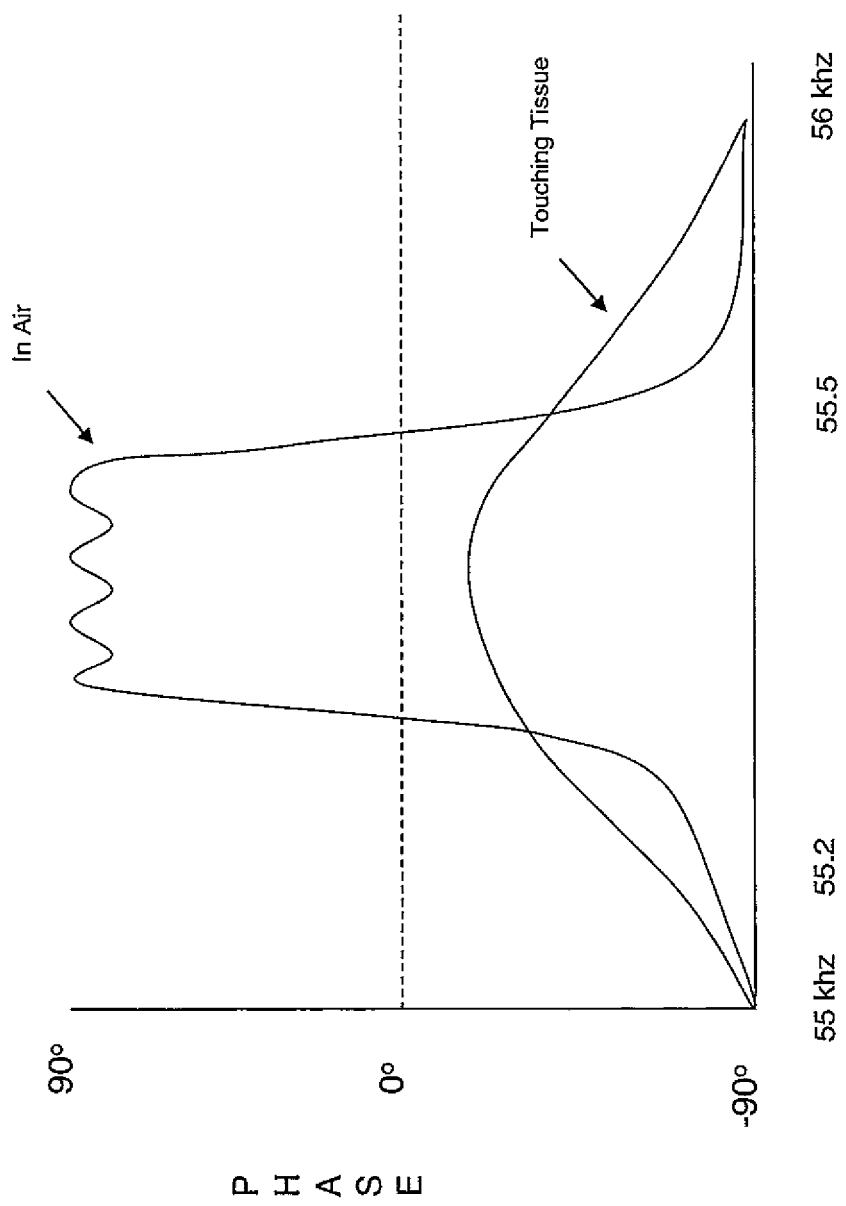
FIG. 16 is a Bode plot depicting the difference in Quality "Q" of an ultrasonic surgical instrument when operating in air and when grasping tissue with respect to phase in accordance with an exemplary embodiment of the present disclosure.

FIGS. 16 and 17 are additional Bode plots depicting the quality or Q of the ultrasonic surgical instrument 250 and comparing the Q when operating at resonance when just in air and when touching tissue. Q is a measure of the quality of the resonance of a system. High quality resonance (high Q) will have a peaked shape, whereas a lower quality resonance (low Q) will have a smaller overall response and a less peaked plot.

As can be seen in both FIGS. 16 and 17, the Q of a resonant structure such as the ultrasonic surgical instrument 250 varies greatly when operating in just air or when in contact with tissue. In fact, the Q will vary depending on a variety of factors regarding the tissue. For example the Q will be different for wet as compared to dry tissue; stiff structures such as bone create a different Q that softer structures such as blood vessels and connective tissue. Even clamping pressure applied to the blade can affect the Q, resulting in a lower Q when clamping pressure is high. Similarly, Q is affected not just by contacting tissue at the end effector 117, but any tissue contact along the length of the resonant structure (e.g., transducer, waveguide and blade) device can change Q. Moreover, contact at nodes has a different effect than contact at an anti-node.

Q may be calculated using the following formula:

$$Q = \frac{f_r}{\Delta f} = \frac{\omega_r}{\Delta \omega},$$

where $f_r$ is the resonant frequency, $\Delta f$ is the bandwidth, $\omega_r = 2\pi f_r$ is the angular resonant frequency, and $\Delta \omega$ is the angular bandwidth. More generally and in the context of reactive component specification (especially inductors), the frequency-dependent definition of Q is used which is as follows:

$$Q\omega = \omega \cdot \frac{Max.EnergyStored}{PowerLoss}.$$

Thus Q may be derived from a plot by measuring the resonant frequency and comparing that plot to the bandwidth at half the energy maximum. Q essentially describes the "peakiness" of the plot. It also can be thought of as how much energy is being dissipated compared to how much is stored in the waveguide. In air an ultrasonic waveguide has a very high Q because almost none of the energy is being dissipated into the air and it is all being stored in the waveguide. When the waveguide touches tissue, the energy dissipates into the tissue, and significantly lowers the Q value meaning that the observed the bandwidth is much wider for a similar resonant frequency. If the waveguide touches metal or water, the Q will also be different depending on how well the waveguide dissipates energy into the metal or water. The more energy dissipated the lower the Q.

In one embodiment of the present disclosure, a variety of Q values are empirically derived and stored in memory of the ultrasonic surgical instrument 250. As the ultrasonic surgical instrument 250 is energized periodic measurement of Q can be undertaken and compared to the values stored in memory. By comparing the measured value to a stored value a signal can be provided to the user regarding the type of material in the end effector 117 at any one time. This may be useful for example to alert the user that there is bone within the end effector 117, or that too much clamping pressure is being applied for the tissue in question, or that a the blade 118 or the waveguide 114 is in contact with metal, from for example another surgical implement or an implant within the patient, or that the waveguide, which may be hot, is in contact with tissue somewhere along its length. Further, the Q value could indicate to the surgeon that the blade 118 is contacting other parts of the end effector (which will be quite stiff) and that such continued contact could damage the ultrasonic surgical instrument 250.

In a further embodiment, the ultrasonic surgical instrument 250 can derive the Q value of the specific tissue grasped within the end effector 117 and adjust the power and drive signal parameters to effectuate better tissue effect. This may be accomplished by considering the Q value of the plot in FIG. 17, where impedance is plotted against the resonant frequency, which indicates the load applied to the blade 118.

In yet a further embodiment, the ultrasonic surgical instrument 250 can monitor the Q value to determine when it changes and upon such a change alter the application of energy (e.g., stop the application of energy) and therewith alter the motion of the blade 118. This may be useful for example in instances where there are layers of tissue having different properties, for example in intestinal surgeries such as enterotomies where it is desirable to cut a first layer of tissue but not cut a second layer of tissue. In such instances, after the initial grasping of the end effector 117 and the application of ultrasonic energy a first Q value can be determined, and then the Q value may be monitored until a change in Q value for the tissue is detected. In some instances the change must be greater than a pre-set amount or percentage, or in other instances any change could result in a stopping of the procedure to prevent the end effector from treating the underlying tissue. Regardless, upon the desired change in Q value the energy applied to the ultrasonic surgical device is altered (e.g., stopped) to prevent further cutting or treatment of tissue.

Although the monitoring of the Q value is described in detail herein, the monitoring and adjusting of the operation of an ultrasonic surgical instrument is not limited to the Q value. Instead other characteristics of the signals that contain information regarding a material in contact with a blade may also be monitored and the energy applied to the blade adjusted in a similar fashion as described herein upon detecting changes and thresholds of that characteristic as described herein with respect to Q values.

In all of the embodiments described herein, the data collected (e.g., resonant frequency data) the calculations made (e.g., temperature or Q value), and other parameters relating to the ultrasonic surgical instrument 250 may be stored locally within a memory such as a EEPROM or other data storage device housed for example within the TAG 256. This data may also be downloadable from the memory such that it can be later analyzed in the event a concern is raised regarding the use of the TAG 256 or other elements of the ultrasonic surgical instrument 250.

Further, although several of the embodiments herein were described specifically with reference to the ultrasonic surgical instrument 250 depicted in FIG. 2A these concepts and control features are equally usable in other ultrasonic surgical systems including, but not limited to, those shown in FIGS. 1, 2 and 3 and described in detail as ultrasonic surgical instrument 300, herein.

Although specific embodiments of the present disclosure have been disclosed, those having ordinary skill in the art will understand that changes may be made to the specific embodiments without departing from the spirit and scope of the disclosure. The scope of the disclosure is not to be restricted, therefore, to the specific embodiments, and it is intended that the appended claims cover any and all such applications, modifications, and embodiments within the scope of the present disclosure.

From the foregoing, and with reference to the various figure drawings, those skilled in the art will appreciate that certain modifications may also be made to the present disclosure without departing from the scope of the same. While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical apparatus comprising:
   a signal generator outputting a drive signal having a frequency;
   an oscillating structure, receiving the drive signal and oscillating at the frequency of the drive signal;
   a plurality of resonators positioned about the oscillating structure and driven by a separate drive signal such that the resonant frequency of each resonator will vary independently from the temperature of each resonator;
   a bridge circuit operably coupled to the plurality of resonators, detecting a mechanical motion for each of the plurality of resonators positioned about the oscillating structure and outputting an electronic signal representative of the mechanical motion for each resonator of the plurality of resonators positioned about the oscillating structure,
   wherein each electronic signal is undistorted by excess heat generated from the mechanical motion of the oscillating structure; and
   a microcontroller receiving each signal output by the bridge circuit, determining an instantaneous frequency at which each resonator of the plurality of resonators positioned about the oscillating structure is oscillating based on each received signal, determining a frequency adjustment necessary to maintain each resonator of the plurality of resonators positioned about the oscillating structure oscillating at a resonance frequency of the oscillating structure, determining a quality (Q value) of each received signal, and determining a type of material contacting each resonator of the plurality of resonators positioned about the oscillating structure based on the determined Q value, wherein the Q value is a frequency-dependent ratio of maximum energy stored to power loss.

2. The apparatus of claim 1, wherein the determined Q values are compared to Q values stored in a memory to determine the type of material in contact with each resonator of the plurality of resonators positioned about the oscillating structure.

3. The apparatus of claim 2, wherein the Q values stored in the memory distinguish between material types selected from the group consisting of wet tissue, dry tissue, dense tissue, bone, and metal objects.

4. The apparatus of claim 2, wherein the determined Q values take into account a clamping pressure applied to the material by an end effector at the end of the oscillating structure.

5. The apparatus of claim 2, wherein upon detecting a specific Q value the ultrasonic surgical apparatus determines that a blade portion of the ultrasonic surgical apparatus is contacting an end effector of the oscillating structure.

6. The apparatus of claim 1, wherein the plurality of resonators create a temperature gradient along the surface of the oscillating structure such that the microcontroller can discern which components of the oscillating structure are being heated, and to what extent they are being heated.

7. A method of determining a type of material an ultrasonic surgical apparatus is contacting, the method comprising:
   generating and supplying a drive signal to a plurality of resonators positioned about an oscillating structure, such that the resonant frequency of each resonator of the plurality of resonators will vary independently from said resonator's temperature;
   detecting a mechanical motion and a temperature variation of each resonator positioned about the oscillating structure;
   generating a plurality of electronic signals representative of the mechanical motion of each resonator positioned about the oscillating structure, wherein each electronic signal is undistorted by excess heat generated from the mechanical motion of the oscillating structure;
   processing the plurality of electronic signals representative of the mechanical motion to determine an instantaneous frequency at which each resonator of the plurality of resonators positioned about the oscillating structure is oscillating based on the plurality of electronic signals representative of the mechanical motion;
   generating a frequency adjustment necessary to maintain the oscillating structure oscillating at a resonance frequency of the oscillating structure; and
   determining a quality (Q value) for each of the plurality of electronic signals representative of the mechanical motion to identify the type of material contacting each resonator of the plurality of resonators positioned about the oscillating structure based on the determined Q value, wherein determining each Q value includes calculating a ratio of frequency to bandwidth.

8. The method of claim 7, wherein the determined Q value for each of the plurality of electronic signals is compared to Q values stored in a memory to determine the type of material in contact with each resonator of the plurality of resonators positioned about the oscillating structure.

9. The method of claim 8, wherein the Q values stored in the memory distinguish between material types selected from the group consisting of wet tissue, dry tissue, dense tissue, bone, and metal objects.

10. The method of claim 8, further comprising, upon detecting a specific Q, determining that a blade portion of the ultrasonic surgical apparatus is contacting an end effector of the ultrasonic surgical apparatus.

11. The method of claim 7, wherein the determined Q value for each of the plurality of electronic signals takes into account a clamping pressure applied to the material by an end effector at the end of the oscillating structure.

12. A method of determining a type of material an ultrasonic surgical apparatus is contacting, the method comprising:
   generating and supplying a drive signal to a plurality of resonators positioned about an oscillating structure, such that the resonant frequency of each resonator of the plurality of resonators will vary independently from said resonator's temperature;
   detecting a mechanical motion and a temperature variation of each resonator positioned about the oscillating structure;
   generating a plurality of electronic signals representative of the mechanical motion of each resonator positioned about the oscillating structure, wherein the signal is undistorted by heat excess generated from the mechanical motion of the oscillating structure;
   processing the plurality of electronic signals representative of the mechanical motion to determine an instantaneous frequency at which each resonator of the plurality of resonators positioned about the oscillating structure is oscillating based on the plurality of electronic signals representative of the mechanical motion;
   generating a frequency adjustment necessary to maintain the oscillating structure oscillating at a resonance frequency of the oscillating structure; and
   determining a quality (Q value) for each of the plurality of electronic signals representative of the mechanical motion to identify the type of material contacting each resonator of the plurality of resonators positioned about the oscillating structure based on the determined Q value, wherein determining the Q value includes deriving the Q value from a plot of impedance against resonant frequency.

13. The method of claim 12, wherein the determined Q value for each of the plurality of electronic signals is compared to Q values stored in a memory to determine the type of material in contact with the oscillating structure.

14. The method of claim 13, wherein the Q values stored in the memory distinguish between material types selected from the group consisting of wet tissue, dry tissue, dense tissue, bone, and metal objects.

15. The method of claim 13, further comprising, upon detecting a specific Q, determining that a blade portion of the ultrasonic surgical apparatus is contacting an end effector of the ultrasonic surgical apparatus.

16. The method of claim 12, wherein the determined Q value for each of the plurality of electronic signals takes into account a clamping pressure applied to the material by an end effector at the end of the oscillating structure.

17. The method of claim 12, further comprising:
   measuring a temperature gradient along the surface of the oscillating structure; and
   determining which components of the oscillating structure are being heated, and to what extent they are being heated.

* * * * *